US009524993B2

(12) United States Patent
Kurokawa

(10) Patent No.: US 9,524,993 B2
(45) Date of Patent: *Dec. 20, 2016

(54) SEMICONDUCTOR DEVICE HAVING A TRANSISTOR WITH AN OXIDE SEMICONDUCTOR LAYER BETWEEN A FIRST GATE ELECTRODE AND A SECOND GATE ELECTRODE

(71) Applicant: Semiconductor Energy Laboratory Co., Ltd., Atsugi-shi, Kanagawa-ken (JP)

(72) Inventor: Yoshiyuki Kurokawa, Sagamihara (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 119 days.

This patent is subject to a terminal disclaimer.

(21) Appl. No.: 14/074,034

(22) Filed: Nov. 7, 2013

(65) Prior Publication Data

US 2014/0061739 A1     Mar. 6, 2014

Related U.S. Application Data

(63) Continuation of application No. 13/021,206, filed on Feb. 4, 2011, now Pat. No. 8,581,170.

(30) Foreign Application Priority Data

Feb. 12, 2010   (JP) .................................. 2010-028970
Mar. 10, 2010   (JP) .................................. 2010-053647

(51) Int. Cl.
*H01L 27/146* (2006.01)
*G06F 3/041* (2006.01)
(Continued)

(52) U.S. Cl.
CPC ........... *H01L 27/146* (2013.01); *G06F 3/0412* (2013.01); *G06K 9/0002* (2013.01);
(Continued)

(58) Field of Classification Search
CPC .................... H01L 27/14643; H01L 27/14609; H01L 21/02554; H01L 21/02565; H01L 27/14603; H01L 29/78606
(Continued)

(56) References Cited

U.S. PATENT DOCUMENTS 5,731,856 A    3/1998   Kim et al.
5,744,864 A    4/1998   Cillessen et al.
(Continued)

FOREIGN PATENT DOCUMENTS

EP    1737044 A    12/2006
EP    2226847 A    9/2010
(Continued)

OTHER PUBLICATIONS

Jeon et al., "180nm Gate Length Amorphous InGaZnO Thin Film Transistor for High Density Image Sensor Applications," IEDM 10: Technical Digest of International Electron Devices Meeting, Dec. 6, 2010, pp. 504-507.
(Continued)

*Primary Examiner* — Que T Le
(74) *Attorney, Agent, or Firm* — Robinson Intellectual Property Law Office; Eric J. Robinson

(57) ABSTRACT

A transistor a gate of which, one of a source and a drain of which, and the other are electrically connected to a selection signal line, an output signal line, and a reference signal line, respectively and a photodiode one of an anode and a cathode of which and the other are electrically connected to a reset signal line and a back gate of the transistor, respectively are included. The photodiode is forward biased to initialize the
(Continued)

back-gate potential of the transistor, the back-gate potential is changed by current of the inversely-biased photodiode flowing in an inverse direction in accordance with the light intensity, and the transistor is turned on to change the potential of the output signal line, so that a signal in accordance with the intensity is obtained.

19 Claims, 16 Drawing Sheets

(51) Int. Cl.
|  |  |
| --- | --- |
| H04N 5/3745 | (2011.01) |
| H04N 1/195 | (2006.01) |
| G06K 9/00 | (2006.01) |
| H01L 29/786 | (2006.01) |
| H01L 27/12 | (2006.01) |
| G09G 3/36 | (2006.01) |
| G02F 1/133 | (2006.01) |
| G02F 1/1333 | (2006.01) |
| A61B 5/117 | (2016.01) |
| G02F 1/1335 | (2006.01) |
| G02F 1/1362 | (2006.01) |
| G02F 1/1368 | (2006.01) |

(52) U.S. Cl.
CPC ....... *G09G 3/3648* (2013.01); *H01L 27/1225* (2013.01); *H01L 27/14632* (2013.01); *H01L 29/7869* (2013.01); *H04N 1/195* (2013.01); *H04N 5/3745* (2013.01); *A61B 5/1172* (2013.01); *G02F 1/13318* (2013.01); *G02F 1/13338* (2013.01); *G02F 1/133512* (2013.01); *G02F 1/133615* (2013.01); *G02F 1/136209* (2013.01); *G02F 2001/13356* (2013.01); *G02F 2001/13685* (2013.01); *G02F 2001/133622* (2013.01); *G09G 2320/0666* (2013.01); *G09G 2360/145* (2013.01); *H01L 27/14643* (2013.01); *H01L 27/14678* (2013.01)

(58) Field of Classification Search
USPC ....... 250/214 R, 208.1, 214.1; 348/294–311; 257/290–292, 440; 327/514, 515
See application file for complete search history.

(56) References Cited

U.S. PATENT DOCUMENTS

| | | |
|---|---|---|
| 6,294,274 B1 | 9/2001 | Kawazoe et al. |
| 6,563,174 B2 | 5/2003 | Kawasaki et al. |
| 6,621,103 B2 | 9/2003 | Yamada |
| 6,642,561 B2 * | 11/2003 | Kakumoto et al. ........... 257/292 |
| 6,727,522 B1 | 4/2004 | Kawasaki et al. |
| 6,747,638 B2 | 6/2004 | Yamazaki et al. |
| 7,049,190 B2 | 5/2006 | Takeda et al. |
| 7,061,014 B2 | 6/2006 | Hosono et al. |
| 7,064,346 B2 | 6/2006 | Kawasaki et al. |
| 7,078,274 B2 | 7/2006 | Yamada |
| 7,105,868 B2 | 9/2006 | Nause et al. |
| 7,211,825 B2 | 5/2007 | Shih et al |
| 7,223,996 B2 | 5/2007 | Yamazaki et al. |
| 7,242,449 B1 | 7/2007 | Yamazaki et al. |
| 7,282,782 B2 | 10/2007 | Hoffman et al. |
| 7,297,977 B2 | 11/2007 | Hoffman et al. |
| 7,323,356 B2 | 1/2008 | Hosono et al. |
| 7,385,224 B2 | 6/2008 | Ishii et al. |
| 7,402,506 B2 | 7/2008 | Levy et al. |
| 7,411,209 B2 | 8/2008 | Endo et al. |
| 7,420,215 B2 | 9/2008 | Inoue et al. |
| 7,453,065 B2 | 11/2008 | Saito et al. |
| 7,453,087 B2 | 11/2008 | Iwasaki |
| 7,462,862 B2 | 12/2008 | Hoffman et al. |
| 7,468,304 B2 | 12/2008 | Kaji et al. |
| 7,501,293 B2 | 3/2009 | Ito et al. |
| 7,525,523 B2 | 4/2009 | Yamazaki et al. |
| 7,663,165 B2 | 2/2010 | Mouli |
| 7,674,650 B2 | 3/2010 | Akimoto et al. |
| 7,732,819 B2 | 6/2010 | Akimoto et al. |
| 7,910,053 B2 | 3/2011 | Inoue et al. |
| 8,094,226 B2 * | 1/2012 | Hattori et al. ................ 348/308 |
| 8,202,365 B2 | 6/2012 | Umeda et al. |
| 8,334,719 B2 | 12/2012 | Koyama et al. |
| 8,748,879 B2 | 6/2014 | Yano et al. |
| 2001/0046027 A1 | 11/2001 | Tai et al. |
| 2002/0056838 A1 | 5/2002 | Ogawa |
| 2002/0132454 A1 | 9/2002 | Ohtsu et al. |
| 2003/0143377 A1 | 7/2003 | Sano et al. |
| 2003/0189401 A1 | 10/2003 | Kido et al. |
| 2003/0218222 A1 | 11/2003 | Wager, III et al. |
| 2004/0038446 A1 | 2/2004 | Takeda et al. |
| 2004/0127038 A1 | 7/2004 | Carcia et al. |
| 2005/0017302 A1 | 1/2005 | Hoffman |
| 2005/0199959 A1 | 9/2005 | Chiang et al. |
| 2006/0035452 A1 | 2/2006 | Carcia et al. |
| 2006/0043377 A1 | 3/2006 | Hoffman et al. |
| 2006/0091793 A1 | 5/2006 | Baude et al. |
| 2006/0108529 A1 | 5/2006 | Saito et al. |
| 2006/0108636 A1 | 5/2006 | Sano et al. |
| 2006/0110867 A1 | 5/2006 | Yabuta et al. |
| 2006/0113536 A1 | 6/2006 | Kumomi et al. |
| 2006/0113539 A1 | 6/2006 | Sano et al. |
| 2006/0113549 A1 | 6/2006 | Den et al. |
| 2006/0113565 A1 | 6/2006 | Abe et al. |
| 2006/0169973 A1 | 8/2006 | Isa et al. |
| 2006/0170111 A1 | 8/2006 | Isa et al. |
| 2006/0197092 A1 | 9/2006 | Hoffman et al. |
| 2006/0208977 A1 | 9/2006 | Kimura |
| 2006/0228974 A1 | 10/2006 | Thelss et al. |
| 2006/0231882 A1 | 10/2006 | Kim et al. |
| 2006/0238135 A1 | 10/2006 | Kimura |
| 2006/0244107 A1 | 11/2006 | Sugihara et al. |
| 2006/0284171 A1 | 12/2006 | Levy et al. |
| 2006/0284172 A1 | 12/2006 | Ishii |
| 2006/0292777 A1 | 12/2006 | Dunbar |
| 2007/0024187 A1 | 2/2007 | Shin et al. |
| 2007/0046191 A1 | 3/2007 | Saito |
| 2007/0052025 A1 | 3/2007 | Yabuta |
| 2007/0054507 A1 | 3/2007 | Kaji et al. |
| 2007/0090365 A1 | 4/2007 | Hayashi et al. |
| 2007/0108446 A1 | 5/2007 | Akimoto |
| 2007/0152217 A1 | 7/2007 | Lai et al. |
| 2007/0172591 A1 | 7/2007 | Seo et al. |
| 2007/0187678 A1 | 8/2007 | Hirao et al. |
| 2007/0187760 A1 | 8/2007 | Furuta et al. |
| 2007/0194379 A1 | 8/2007 | Hosono et al. |
| 2007/0252928 A1 | 11/2007 | Ito et al. |
| 2007/0272922 A1 | 11/2007 | Kim et al. |
| 2007/0287296 A1 | 12/2007 | Chang |
| 2008/0006877 A1 | 1/2008 | Mardilovich et al. |
| 2008/0038882 A1 | 2/2008 | Takechi et al. |
| 2008/0038929 A1 | 2/2008 | Chang |
| 2008/0050595 A1 | 2/2008 | Nakagawara et al. |
| 2008/0073653 A1 | 3/2008 | Iwasaki |
| 2008/0083950 A1 | 4/2008 | Pan et al. |
| 2008/0106191 A1 | 5/2008 | Kawase |
| 2008/0128689 A1 | 6/2008 | Lee et al. |
| 2008/0129195 A1 | 6/2008 | Ishizaki et al. |
| 2008/0166834 A1 | 7/2008 | Kim et al. |
| 2008/0182358 A1 | 7/2008 | Cowdery-Corvan et al. |
| 2008/0224133 A1 | 9/2008 | Park et al. |
| 2008/0254569 A1 | 10/2008 | Hoffman et al. |
| 2008/0258139 A1 | 10/2008 | Ito et al. |
| 2008/0258140 A1 | 10/2008 | Lee et al. |
| 2008/0258141 A1 | 10/2008 | Park et al. |
| 2008/0258143 A1 | 10/2008 | Kim et al. |
| 2008/0296568 A1 | 12/2008 | Ryu et al. |
| 2009/0068773 A1 | 3/2009 | Lai et al. |
| 2009/0073325 A1 | 3/2009 | Kuwabara et al. |
| 2009/0076322 A1 | 3/2009 | Matsunaga et al. |
| 2009/0101948 A1 | 4/2009 | Park et al. |
| 2009/0114910 A1 | 5/2009 | Chang |

(56) References Cited

U.S. PATENT DOCUMENTS

| | | |
|---|---|---|
| 2009/0134399 A1 | 5/2009 | Sakakura et al. |
| 2009/0152506 A1 | 6/2009 | Umeda et al. |
| 2009/0152541 A1 | 6/2009 | Maekawa et al. |
| 2009/0261389 A1 | 10/2009 | Cho et al. |
| 2009/0278122 A1 | 11/2009 | Hosono et al. |
| 2009/0280600 A1 | 11/2009 | Hosono et al. |
| 2009/0295769 A1 | 12/2009 | Yamazaki et al. |
| 2010/0065844 A1 | 3/2010 | Tokunaga |
| 2010/0092800 A1 | 4/2010 | Itagaki et al. |
| 2010/0109002 A1 | 5/2010 | Itagaki et al. |
| 2010/0182282 A1 | 7/2010 | Kurokawa et al. |
| 2011/0176038 A1 | 7/2011 | Kurokawa et al. |
| 2011/0198483 A1 | 8/2011 | Kurokawa |

FOREIGN PATENT DOCUMENTS

| | | |
|---|---|---|
| JP | 60-198861 A | 10/1985 |
| JP | 63-210022 A | 8/1988 |
| JP | 63-210023 A | 8/1988 |
| JP | 63-210024 A | 8/1988 |
| JP | 63-215519 A | 9/1988 |
| JP | 63-239117 A | 10/1988 |
| JP | 63-265818 A | 11/1988 |
| JP | 02-180071 A | 7/1990 |
| JP | 05-251705 A | 9/1993 |
| JP | 08-264794 A | 10/1996 |
| JP | 11-505377 | 5/1999 |
| JP | 11-274451 A | 10/1999 |
| JP | 2000-044236 A | 2/2000 |
| JP | 2000-150900 A | 5/2000 |
| JP | 2001-109394 A | 4/2001 |
| JP | 2001-160299 A | 6/2001 |
| JP | 2001-292276 A | 10/2001 |
| JP | 2002-076356 A | 3/2002 |
| JP | 2002-289859 A | 10/2002 |
| JP | 2003-086000 A | 3/2003 |
| JP | 2003-086808 A | 3/2003 |
| JP | 2004-103957 A | 4/2004 |
| JP | 2004-273614 A | 9/2004 |
| JP | 2004-273732 A | 9/2004 |
| JP | 2005-005421 A | 1/2005 |
| JP | 2005-183921 A | 7/2005 |
| JP | 2009-089351 A | 4/2009 |
| JP | 2009-105381 A | 5/2009 |
| JP | 2009-147056 A | 7/2009 |
| JP | 2009-167087 A | 7/2009 |
| JP | 2009-535819 | 10/2009 |
| JP | 2009-260254 A | 11/2009 |
| JP | 2010-016072 A | 1/2010 |
| TW | 550821 | 9/2003 |
| TW | 594336 | 6/2004 |
| TW | I269448 | 12/2006 |
| TW | I333281 | 11/2010 |
| WO | WO-2004/114391 | 12/2004 |
| WO | WO-2008/027392 | 3/2008 |
| WO | WO-2008/136505 | 11/2008 |

OTHER PUBLICATIONS

International Search Report (Application No. PCT/JP2011/051034) Dated Apr. 26, 2011.

Written Opinion (Application No. PCT/JP2011/051034) Dated Apr. 26, 2011.

Taiwanese Office Action (Application No. 100102858) Dated Oct. 20, 2015.

Asakuma.N et al., "Crystallization and Reduction of Sol-Gel-Derived Zinc Oxide Films by Irradiation with Ultraviolet Lamp", Journal of Sol-Gel Science and Technology, 2003, vol. 26, pp. 181-184.

Asaoka.Y et al., "29.1:Polarizer-Free Reflective LCD Combined with Ultra Low-Power Driving Technology", SID Digest '09: SID International Symposium Digest of Technical Papers, May 31, 2009, pp. 395-398.

Chern.H et al., "An Analytical Model for the Above-Threshold Characteristics of Polysilicon Thin-Film Transistors", IEEE Transactions on Electron Devices, Jul. 1, 1995, vol. 42, No. 7, pp. 1240-1246.

Cho.D et al., "21.2:Al and Sn-Doped Zinc Indium Oxide Thin Film Transistors for Amoled Back-Plane", SID Digest '09: SID International Symposium Digest of Technical Papers, May 31, 2009, pp. 280-283.

Clark.S et al., "First Principles Methods Using Castep", Zeitschrift fur Kristallographie, 2005, vol. 220, pp. 567-570.

Coates.D et al., "Optical Studies of the Amorphous Liquid-Cholesteric Liquid Crystal Transition: The "Blue Phase"", Physics Letter, Sep. 10, 1973, vol. 45A, No. 2, pp. 115-116.

Costello.M et al., "Electron Microscopy of a Cholesteric Liquid Crystal and Its Blue Phase", Phys. Rev. A (Physical Review. A), May 1, 1984, vol. 29, No. 5, pp. 2957-2959.

Dembo.H et al., "RFCPUS on Glass and Plastic Substrates Fabricated by TFT Transfer Technology", IEDM 05: Technical Digest of International Electron Devices Meeting, Dec. 5, 2005, pp. 1067-1069.

Fortunato.E et al., "Wide-Bandgap High-Mobility ZNO Thin-Film Transistors Produced at Room Temperature", Appl. Phys. Lett. (Applied Physics Letters), Sep. 27, 2004, vol. 85, No. 13, pp. 2541-2543.

Fung.T et al., "2-D Numerical Simulation of High Performance Amorphous In—Ga—Zn—O TFTs for Flat Panel Displays", AM-FPD '08 Digest of Technical Papers, Jul. 2, 2008, pp. 251-252, The Japan Society of Applied Physics.

Godo.H et al., "P-9: Numerical Analysis on Temperature Dependence of Characteristics of Amorphous In—Ga—Zn-Oxide TFT", SID Digest '09: SID International Symposium Digest of Technical Papers, May 31, 2009, pp. 1110-1112.

Godo.H et al., "Temperature Dependence of Characteristics and Electronic Structure for Amorphous In—Ga—Zn-Oxide TFT", AM-FPD '09 Digest of Technical Papers, Jul. 1, 2009, pp. 41-44.

Hayashi.R et al., "42.1: Invited Paper: Improved Amorphous In—Ga—Zn—0 TFTs", SID Digest '08: SID International Symposium Digest of Technical Papers, May 20, 2008, vol. 39, pp. 621-624.

Hirao.T et al., "Novel Top-Gate Zinc Oxide Thin-Film Transistors (ZNO TFTs) for AMLCDS", J. Soc. Inf. Display (Journal of the Society for information Display), 2007, vol. 15, No. 1, pp. 17-22.

Hosono.H et al., "Working hypothesis to explore novel wide band gap electrically conducting amorphous oxides and examples", J. Non-Cryst. Solids (Journal of Non-Crystalline Solids), 1996, vol. 198-200, pp. 165-169.

Hosono.H, "68.3: Invited Paper:Transparent Amorphous Oxide Semiconductors for High Performance TFT", SID Digest '07: SID International Symposium Digest of Technical Papers, 2007, vol. 38, pp. 1830-1833.

Hsieh.H et al., "P-29: Modeling of Amorphous Oxide Semiconductor Thin Film Transistors and Subgap Density of States", SID Digest '08: SID International Symposium Digest of Technical Papers, May 20, 2008, vol. 39, pp. 1277-1280.

Ikeda.T et al., "Full-Functional System Liquid Crystal Display Using Cg-Silicon Technology", SID Digest '08:SID International Symposium Digest of Technical Papers, 2004, vol. 35, pp. 860-863.

Janotti.A et al., "Native Point Defects in ZnO", Phys. Rev. B (Physical Review. B), Oct. 4, 2007, vol. 76, No. 16, pp. 165202-1-165202-22.

Janotti.A et al., "Oxygem Vacancies In ZnO", Appl. Phys. Lett. (Applied Physics Letters) , 2005, vol. 87, pp. 122102-1-122102-3.

Jeong.J et al., "3.1: Distinguished Paper: 12.1-Inch WXGA AMOLED Display Driven by Indium-Gallium-Zinc Oxide TFTs Array", SID Digest '08: SID International Symposium Digest of Technical Papers, May 20, 2008, vol. 39, No. 1, pp. 1-4.

Jin.D et al., "65.2: Distinguished Paper: World-Largest (6.5") Flexible Full Color Top Emission AMOLED Display on Plastic Film and its Bending Properties", SID Digest '09: SID International Symposium Digest of Technical Papers, May 31, 2009, pp. 983-985.

Kanno.H et al., "White Stacked Electrophosphorecent Organic Light-Emitting Devices Employing MOO3 as a Charge-Generation Layer", Adv. Mater. (Advanced Materials), 2006, vol. 18, No. 3, pp. 339-342.

(56) References Cited

OTHER PUBLICATIONS

Kikuchi.H et al., "39.1: Invited Paper: Optically Isotropic Nano-Structured Liquid Crystal Composites for Display Applications", SID Digest '09: SID International Symposium Digest of Technical Papers, May 31, 2009, pp. 578-581.

Kikuchi.H et al., "62.2: Invited Paper:Fast Electro-Optical Switching in Polymer-Stabilized Liquid Crystalline Blue Phases for Display Applications", SID Digest '07:SID International Symposium Digest of Technical Papers, 2007, vol. 38, pp. 1737-1740.

Kikuchi.H et al., "Polymer-Stabilized Liquid Crystal Blue Phases", Nature Materials, Sep. 2, 2002, vol. 1, pp. 64-68.

Kim.S et al., "High-Performance oxide thin film transistors passivated by various gas plasmas", 214th ECS Meeting, 2008, No. 2317, ECS.

Kimizuka.N et al., "Spinel, YBFE2O4, and YB2FE3O7 Types of Structures for Compounds in the IN2O3 and SC2O3—A2O3—BO Systems [A; Fe, Ga; Or Al; B: Mg, Mc, Fe, Ni, Cu, Or Zn] at Temperatures over 1000° C", Journal of Solid State Chemistry, 1985, vol. 600, pp. 382-384.

Kimizuka.N et al., "Syntheses and Single-Crystal Data of Homologous Compounds, In2O3(ZnO)m (m= 3, 4, and 5), InGaO3(ZnO)3, and Ga2O3(ZnO)m (m=7, 8, 9, and 16) in the In2O3—ZnGa2O4—ZnO System", Journal of Solid State Chemistry, Apr. 1, 1995, vol. 116, No. 1, pp. 170-178.

Kitzerow.H et al., "Observation of Blue Phases in Chiral Networks", Liquid Crystals, 1993, vol. 14, No. 3, pp. 911-916.

Kurokawa.Y et al., "UHF RFCPUS on Flexible and Glass Substrates for Secure RFID Systems", Journal of Solid-State Circuits, 2008, vol. 43, No. 1, pp. 292-299.

Lany.S et al., "Dopability, Intrinsic Conductivity, and Nonstoichiometry of Transparent Conducting Oxides", Phys. Rev. Lett. (Physical Review Letters), Jan. 26, 2007, vol. 98, pp. 045501-1-045501-4.

Lee.H et al., "Current Status of, Challenges to, and Perspective View of AM-OLED", IDW '06: Proceedings of the 13th International Display Workshops, Dec. 7, 2006, pp. 663-666.

Lee.J et al., "World'S Largest (15-Inch) XGA AMLCD Panel Using IGZO Oxide TFT", SID Digest '08: SID International Symposium Digest of Technical Papers, May 20, 2008, vol. 39, pp. 625-628.

Lee.M et al., "15.4:Excellent Performance of Indium-Oxide-Based Thin-Film Transistors by DC Sputtering", SID Digest '09: SID International Symposium Digest of Technical Papers, May 31, 2009, pp. 191-193.

Li.C et al., "Modulated Structures of Homologous Compounds InMO3(ZnO)m (M=In,Ga; m=Integer) Described by Four-Dimensional Superspace Group", Journal of Solid State Chemistry, 1998, vol. 139, pp. 347-355.

Masuda.S et al., "Transparent thin film transistors using ZnO as an active channel layer and their electrical properties", J. Appl. Phys. (Journal of Applied Physics), Feb. 1, 2003, vol. 93, No. 3, pp. 1624-1630.

Meiboom.S et al., "Theory of the Blue Phase of Cholesteric Liquid Crystals", Phys. Rev. Lett. (Physical Review Letters), May 4, 1981, vol. 46, No. 18, pp. 1216-1219.

Miyasaka.M, "Suftla Flexible Microelectronics on Their Way to Business", SID Digest '07: SID International Symposium Digest of Technical Papers, 2007, vol. 38, pp. 1673-1676.

Mo.Y et al., "Amorphous Oxide TFT Backplanes for Large Size AMOLED Displays", IDW '08: Proceedings of the 6TH International Display Workshops, Dec. 3, 2008, pp. 581-584.

Nakamura.M et al., "The phase relations in the In2O3—Ga2ZnO4—ZnO system at 1350°C", Journal of Solid State Chemistry, Aug. 1, 1991, vol. 93, No, 2, pp. 298-315.

Nakamura.M, "Synthesis of Homologous Compound with New Long-Period Structure", NIRIM Newsletter, Mar. 1, 1995, vol. 150, pp. 1-4.

Nomura.K et al., "Amorphous Oxide Semiconductors for High-Performance Flexible Thin-Film Transistors", Jpn. J. Appl. Phys. (Japanese Journal of Applied Physics), 2006, vol. 45, No. 5B, pp. 4303-4308.

Nomura.K et al., "Carrier transport in transparent oxide semiconductor with intrinsic structural randomness probed using single-crystalline InGaO3(ZnO)5 films", Appl. Phys. Lett. (Applied Physics Letters), Sep. 13, 2004, vol. 85, No. 11, pp. 1993-1995.

Nomura.K et al., "Room-Temperature Fabrication of Transparent Flexible Thin-Film Transistors Using Amorphous Oxide Semiconductors", Nature, Nov. 25, 2005, Vol. 432, pp. 488-492.

Nomura.K et al., "Thin-Film Transistor Fabricated in Single-Crystalline Transparent Oxide Semiconductor", Science, May 23, 2003, vol. 300, No. 5623, pp. 1269-1272.

Nowatari.H et al., "60.2: Intermediate Connector With Suppressed Voltage Loss for White Tandem OLEDS", SID Digest '09: SID International Symposium Digest of Technical Papers, May 31, 2009, vol. 40, pp. 899-902.

Oba.F et al., "Defect energetics in ZnO: A hybrid Hartree-Fock density functional study", Phys. Rev. B (Physical Review. B), 2008, vol. 77, pp. 245202-1-245202-6.

Oh.M et al., "Improving the Gate Stability of ZnO Thin-Film Transistors With Aluminum Oxide Dielectric Layers", J. Electrochem. Soc. (Journal of the Electrochemical Society), 2008, vol. 155, No. 12, pp. H1009-H1014.

Ohara.H et al., "21.3:4.0 in. QVGA AMOLED Display Using In—Ga—Zn-Oxide TFTs With a Novel Passivation Layer", SID Digest '09: SID International Symposium Digest of Technical Papers, May 31, 2009, pp. 284-287.

Ohara.H et al., "Amorphous In—Ga—Zn-Oxide TFTs with Suppressed Variation for 4.0 inch QVGA AMOLED Display", AM-FPD '09 Digest of Technical Papers, Jul. 1, 2009, pp. 227-230, the Japan Society of Applied Physics.

Orita.M et al., "Amorphous transparent conductive oxide InGaO3(ZnO)m (m <4):a Zn4s conductor", Philosophical Magazine, 2001, vol. 81, No. 5, pp. 501-515.

Orita.M et al., "Mechanism of Electrical Conductivity of Transparent InGaZnO4", Phys. Rev. B (Physical Review. B), Jan. 15, 2000, vol. 61, No. 3, pp. 1811-1816.

Osada.T et al., "15.2: Development of Driver-Integrated Panel using Amorphous In—Ga—Zn-Oxide TFT", SID Digest '09 : SID International Symposium Digest of Technical Papers, May 31, 2009, pp. 184-187.

Osada.T et al., "Development of Driver-Integrated Panel Using Amorphous In—Ga—Zn-Oxide TFT", AM-FPD '09 Digest of Technical Papers, Jul. 1, 2009, pp. 33-36.

Park.J et al., "Amorphous Indium-Gallium-Zinc Oxide TFTs and Their Application for Large Size AMOLED", AM-FPD '08 Digest of Technical Papers, Jul. 2, 2008, pp. 275-278.

Park.J et al., "Dry etching of ZnO films and plasma-Induced damage to optical properties", J. Vac. Sci. Technol. B (Journal of Vacuum Science & Technology B), Mar. 1, 2003, vol. 21, No. 2, pp. 800-803.

Park.J et al., "Electronic Transport Properties of Amorphous Indium-Gallium-Zinc Oxide Semiconductor Upon Exposure to Water", Appl. Phys. Lett. (Applied Physics Letters), 2008, vol. 92, pp. 072104-1-072104-3.

Park.J et al., "High performance amorphous oxide thin film transistors with self-aligned top-gate structure", IEDM 09: Technical Digest of International Electron Devices Meeting, Dec. 7, 2009, pp. 191-194.

Park.J et al., "Improvements in the Device Characteristics of Amorphous Indium Gallium Zinc Oxide Thin-Film Transistors by Ar Plasma Treatment", Appl. Phys. Lett. (Applied Physics Letters), Jun. 26, 2007, vol. 90, No. 26, pp. 262106-1-262106-3.

Park.S et al., "Challenge to Future Displays: Transparent AM-OLED Driven by Peald Grown ZnO TFT", IMID '07 Digest, 2007, pp. 1249-1252.

Park.Sang-Hee et al., "42.3: Transparent ZnO Thin Film Transistor for the Application of High Aperture Ratio Bottom Emission AM-OLED Display", SID Digest '08: SID International Symposium Digest of Technical Papers, May 20, 2008, vol. 39, pp. 629-632.

Prins.M et al., "A Ferroelectric Transparent Thin-Film Transistor", Appl. Phys. Lett. (Applied Physics Letters), Jun. 17, 1996, vol. 68, No. 25, pp. 3650-3652.

(56) References Cited

OTHER PUBLICATIONS

Sakata.J et al., "Development of 4.0-IN. AMOLED Display With Driver Circuit Using Amorphous In—Ga—Zn-Oxide TFTs", IDW '09: Proceedings of the 16th International Display Workshops, 2009, pp. 689-692.

Son.K et al., "42.4L: Late-News Paper: 4 Inch QVGA AMOLED Driven by the Threshold Voltage Controlled Amorphous GIZO (Ga2O3—In2O3—ZnO) TFT", SID Digest '08: SID International Symposium Digest of Technical Papers, May 20, 2008, Vol. 39, pp. 633-636.

Takahashi.M et al., "Theoretical Analysis of IGZO Transparent Amorphous Oxide Semiconductor", IDW '08: Proceedings of the 15th International Display Workshops, Dec. 3, 2008, pp. 1637-1640.

Tsuda.K et al., "Ultra Low Power Consumption Technologies for Mobile TFT-LCDs ", IDW '02: Proceedings of the 9th International Display Workshops, Dec. 4, 2002, pp. 295-298.

Ueno.K et al., "Field-Effect Transistor on SrTiO3 with Sputtered Al2O3 Gate Insulator", Appl. Phys. Lett. (Applied Physics Letters), Sep. 1, 2003, vol. 83, No. 9, pp. 1755-1757.

Van de Walle.C, "Hydrogen as a Cause of Doping in Zinc Oxide", Phys. Rev. Lett. (Physical Review Letters), Jul. 31, 2000, vol. 85, No. 5, pp. 1012-1015.

\* cited by examiner

SEMICONDUCTOR DEVICE HAVING A TRANSISTOR WITH AN OXIDE SEMICONDUCTOR LAYER BETWEEN A FIRST GATE ELECTRODE AND A SECOND GATE ELECTRODE

TECHNICAL FIELD

Embodiments of the present invention relate to a semiconductor device in which pixels having a photosensor are arranged in matrix and to a driving method thereof. Further, an embodiment of the present invention relates to an electronic appliance having the semiconductor device.

BACKGROUND ART

A semiconductor device in this specification refers to any device that can function by utilizing semiconductor characteristics; electro-optic devices, semiconductor circuits, and electronic appliances are all semiconductor devices.

In recent years, a semiconductor device having a sensing element for detecting light (also called a "photosensor") has drawn attention. As examples of the semiconductor device having a photosensor, a CCD image sensor, a CMOS image sensor, and the like can be given. They are used in electronic appliances equipped with an image pick-up function such as a digital still camera and a mobile phone.

A semiconductor device having a photosensor in a display region, which can detect a touch of an object (e.g., a pencil, a finger) on the display region, is also called a touch panel, a touch screen, or the like (hereinafter simply called a "touch panel"). Such a photosensor provided in the display region of the semiconductor device enables the display region to double as an input region; as an example, a semiconductor device equipped with an image loading function has been disclosed in Patent Document 1.

REFERENCE

Patent Document 1: Japanese Published Patent Application No. 2001-292276

DISCLOSURE OF INVENTION

In order to pick up an image of an object at high resolution with the above-described semiconductor device, it is necessary to densely integrate minute light-receiving elements. Contraction of design rules causes deterioration of sensitivity of receiving light due to area reduction of a light-receiving portion of a light-receiving element (photodiode), leading to noise at the time of image pick-up.

In addition, the semiconductor device having a photosensor in a display region has had a problem in that an area occupied by a display element is small and the display quality is insufficient because a display element portion for displaying an image and a photosensor portion for detecting an object are both provided in a pixel.

In this specification, the photosensor refers to a sensing element (including a photodiode and a transistor), and the photosensor portion refers to a region in which the sensing element is provided.

Therefore, it is desired that the number of transistors included in the photosensor is decreased to decrease the area occupied by the photosensor portion. An area reduced in accordance with a reduction of the number of transistors can be allocated to a light-receiving element or a display element.

Further, large off-state current of a transistor may decrease the dynamic range of the image pick-up function; thus, it is desired that the off-state current of the transistor included in the photosensor is small.

In view of the above, it is an object of one embodiment of the present invention to provide a semiconductor device equipped with a high-quality image pick-up function or a high-quality display function, in which the photosensor portion occupies a small area.

One embodiment of the present invention relates to a display device or a semiconductor device in which a photosensor includes one photodiode and one or two transistor (s) in which the threshold voltage can be changed by changing the potential of a back gate thereof and the off-state current is extremely small.

One embodiment of the present invention is a semiconductor device including a first transistor and a photodiode, in which a gate of the first transistor is electrically connected to a selection signal line, one of a source and a drain of the same is electrically connected to an output signal line, the other of the source and the drain is electrically connected to a reference signal line, one of an anode and a cathode of the photodiode is electrically connected to a reset signal line, and the other of the anode and the cathode is electrically connected to a back gate of the first transistor.

One embodiment of the present invention is a semiconductor device including a display element portion formed in a pixel in a display region and a photosensor portion including a first transistor and a photodiode, in which a gate of the first transistor is electrically connected to a selection signal line, one of a source and a drain of the same is electrically connected to an output signal line, the other of the source and the drain is electrically connected to a reference signal line, one of an anode and a cathode of the photodiode is electrically connected to a reset signal line, and the other of the anode and the cathode is electrically connected to a back gate of the first transistor.

In the above-described structure, a second transistor one of a source and a drain of which is electrically connected to the other of the anode and the cathode of the photodiode and the other of the source and the drain of which is electrically connected to the back gate of the first transistor may be provided.

A PN photodiode or a PIN photodiode using a silicon semiconductor can be used as the photodiode. In particular, it is preferable to use a PIN photodiode in which an i-type semiconductor layer is formed using an amorphous silicon semiconductor that has light absorption property in a wavelength region close to the human luminosity factor.

Further, the photodiode may be provided so as to overlap parts of the first transistor and the second transistor, whereby the area of the photosensor portion can be decreased. Alternatively, the light reception area of the photodiode can be increased.

It is preferable to use a transistor using a highly purified oxide semiconductor in which the number of carriers is extremely small as any of the first and second transistors, though a transistor using a silicon semiconductor can be used as well. In such a transistor including an oxide semiconductor layer, the off-state current density per micrometer in a channel width at room temperature can be suppressed to less than or equal to 10 aA/μm ($1\times10^{-17}$ A/μm), further less than or equal to 1 aA/μm ($1\times10^{-18}$ A/μm), or still further less than or equal to 10 zA/μm ($1\times10^{-20}$ A/μm). Accordingly, unnecessary potential output to the output signal line can be suppressed in the photosensor of one embodiment of the present invention.

One embodiment of the present invention is a driving method of a semiconductor device including a photodiode, a first transistor whose back gate is electrically connected to one of an anode and a cathode of the photodiode, a reset signal line which is electrically connected to the other of the anode and the cathode of the photodiode, a selection signal line which is electrically connected to a gate of the first transistor, an output signal line which is electrically connected to one of a source and a drain of the first transistor, and a reference signal line which is electrically connected to the other of the source and the drain of the first transistor. The potential of the reset signal line is set at a potential which makes the photodiode forward biased to initialize the potential of the back gate; the potential of the reset signal line is set at a potential which makes the photodiode inversely biased; the potential of the back gate is changed by a current of the photodiode flowing in the inverse direction in accordance with the intensity of light; the potential of the selection signal line is set at a potential at which the first transistor is turned on to change the potential of the output signal line; the potential of the selection signal line is set at a potential at which the first transistor is turned off to retain the potential of the output signal line; and the potential of the output signal line is output to a circuit which is electrically connected to the output signal line.

One embodiment of the present invention is a driving method of a semiconductor device including a photodiode, a first transistor having a back gate, a second transistor one of a source and a drain of which is electrically connected to one of an anode and a cathode of the photodiode and the other of the source and the drain of which is electrically connected to the back gate of the first transistor, a reset signal line which is electrically connected to the other of the anode and the cathode of the photodiode, a selection signal line which is electrically connected to a gate of the first transistor, an output signal line which is electrically connected to one of a source and a drain of the first transistor, a reference signal line which is electrically connected to the other of the source and the drain of the first transistor, and a gate signal line which is electrically connected to a gate of the second transistor. The potential of the reset signal line is set at a potential which makes the photodiode forward biased; the potential of the gate signal line is set at a potential at which the second transistor is turned on to initialize the potential of the back gate; the potential of the reset signal line is set at a potential which makes the photodiode inversely biased; the potential of the back gate is changed by a current of the photodiode flowing in the inverse direction in accordance with the intensity of light; the potential of the gate signal line is set at a potential at which the second transistor is turned off to retain the potential of the back gate; the potential of the selection signal line is set at a potential at which the first transistor is turned on to change the potential of the output signal line; the potential of the selection signal line is set at a potential at which the first transistor is turned off to retain the potential of the output signal line; and the potential of the output signal line is output to a circuit which is electrically connected to the output signal line.

As the first transistor, a transistor whose threshold voltage can be changed by a potential supplied to the back gate thereof is used. The potential of the back gate can be changed in accordance with the light intensity of the irradiation on the photodiode which is electrically connected to a back-gate signal line. Accordingly, the threshold voltage of the transistor can be changed to adjust the potential of the output signal line.

According to one embodiment of the present invention, a semiconductor device equipped with a high-quality image pick-up function and/or a high-quality display function with high resolution and with less noise can be provided.

BEST MODE FOR CARRYING OUT THE INVENTION

Figure 1A:
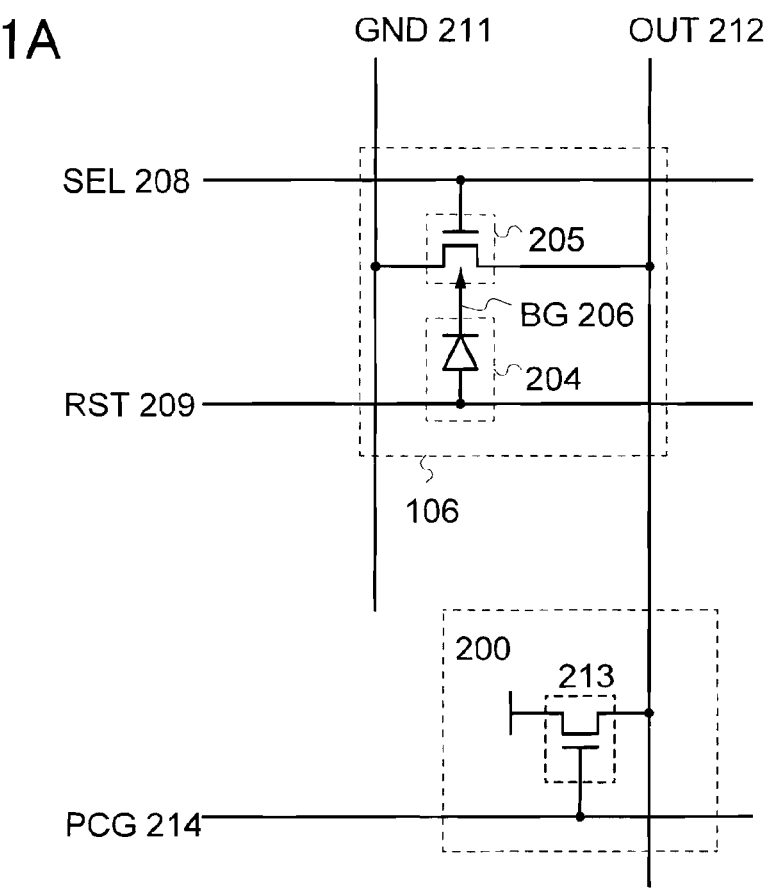
FIG. 1A is a diagram illustrating a configuration of a photosensor according to one embodiment of the present invention.

Embodiments and Examples of the present invention will be described below with reference to the accompanying drawings. Note that the present invention is not limited to the following description, and it is easily understood by those skilled in the art that modes and details disclosed herein can be modified in various ways. Therefore, the present invention is not construed as being limited to the content of the embodiments disclosed herein. In the structures according to embodiments and examples described below, the same portions or portions having similar functions are denoted by the same reference numerals throughout the drawings, and description of such portions is not repeated.

(Embodiment 1)

In Embodiment 1, one example of a semiconductor device according to one embodiment of the present invention will be described using drawings.

FIG. 1A illustrates a configuration for one pixel, of photosensors arranged in pixel matrix of a semiconductor device equipped with an image pick-up function, which includes a photodiode 204 and a transistor 205.

An anode of the photodiode 204 is electrically connected to a photodiode reset signal line (hereinafter referred to as a reset signal line) 209, and a cathode thereof is electrically connected to a back-gate signal line 206. One of a source and a drain of the transistor 205, the other of the source and the drain thereof, a gate thereof, and a back gate thereof are electrically connected to a photosensor reference signal line (hereinafter referred to as a reference signal line) 211, a photosensor output signal line (hereinafter referred to as an output signal line) 212, a gate signal line (hereinafter referred to as a selection signal line) 208, and the back-gate signal line 206, respectively.

In this embodiment, elements included in a photosensor portion 106 are one transistor and one photodiode, whereby the area of the photosensor portion can be extremely small. One embodiment of the present invention features this structure. A precharge circuit 200, which is shown in FIG. 1A for clear explanation made later of an example of an operation, is not necessarily provided; resistive dividing or the like may be employed.

Configurations of conventional photosensors include three or four transistors in addition to a photodiode. A configuration and an operation of a photosensor using three transistors are described as a conventional example, below.

Figure 2A:
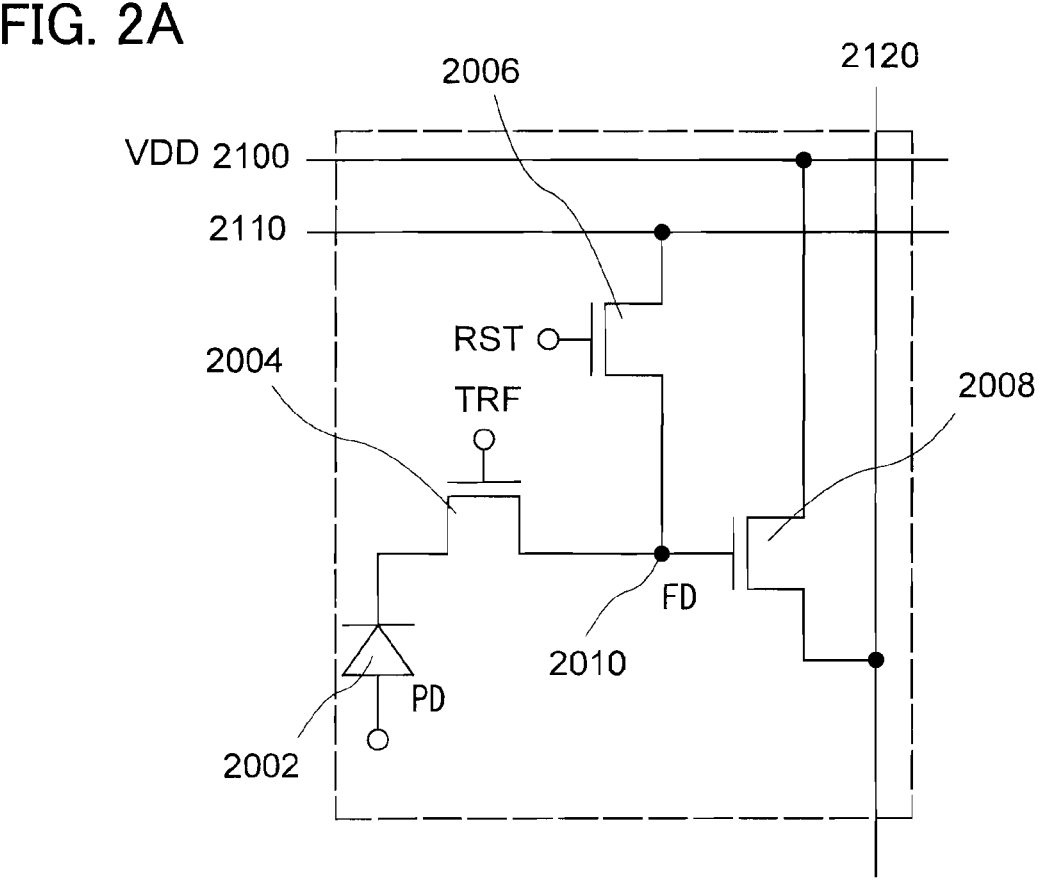
FIG. 2A is a diagram illustrating a configuration of a conventional photosensor.

FIG. 2A is a diagram of a conventional example of a photosensor using three transistors. The photosensor includes a photodiode 2002, a transfer transistor 2004, a reset transistor 2006, an amplification transistor 2008, and a variety of wirings.

The photodiode 2002 is connected to one of a source side and a drain side of the transfer transistor 2004, and a signal charge accumulation portion 2010 (also called a floating diffusion (FD)) is formed on the other of the source side and the drain side of the transfer transistor 2004. The signal charge accumulation portion 2010 is connected to one of a source side and a drain side of the reset transistor 2006 and a gate of the amplification transistor 2008. A selection transistor is further connected to the amplification transistor in some cases, resulting in a configuration using four transistors.

Figure 2B:
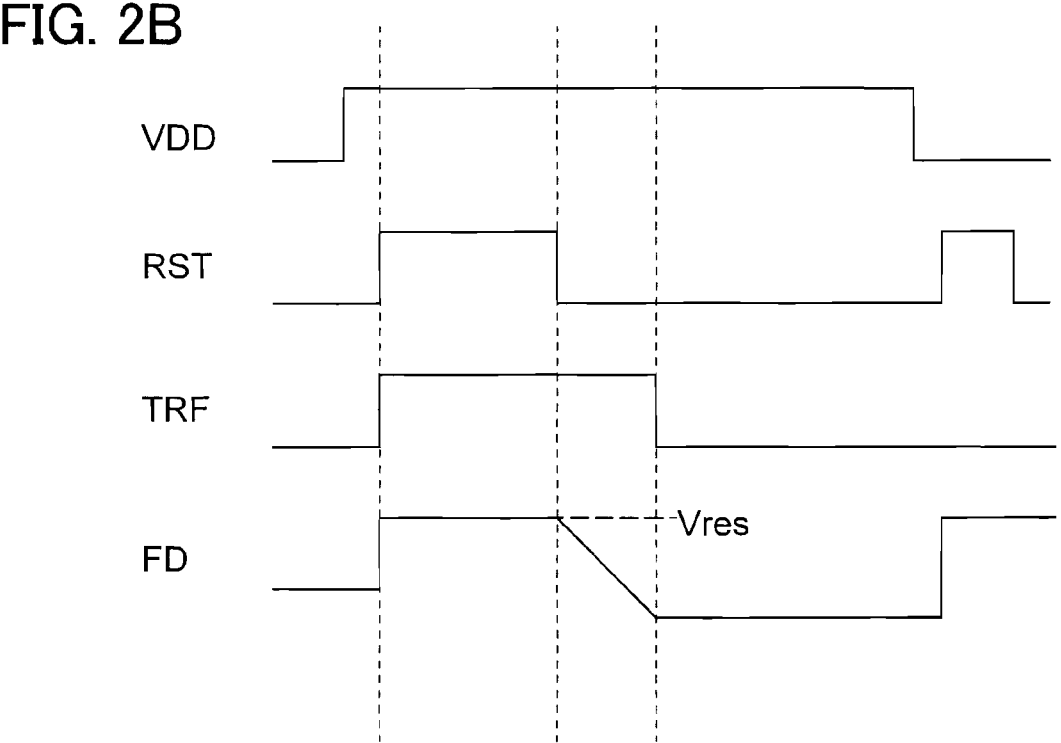
FIG. 2B is a timing chart thereof.

Next, an operation of the photosensor is described using a timing chart in FIG. 2B. First, a power source potential is supplied to a power source line 2100 (VDD). Then, a transfer signal (TRF) is input to a gate of the transfer transistor 2004 to turn on the transfer transistor 2004, and a reset signal (RST) is input to a gate of the reset transistor 2006 to turn on the reset transistor 2006. At that time, the signal charge accumulation portion 2010 (FD) and a cathode of the photodiode 2002 have the potential of a reset power source line 2110. After that, the reset transistor 2006 is turned off, and a current of the photodiode 2002 flows in accordance with the light intensity to lower the potential of the signal charge accumulation portion 2010 (FD). Then, the transfer transistor 2004 is turned off, and the potential of the signal charge accumulation portion 2010 (FD) at that time is retained in the signal charge accumulation portion 2010 (FD). Then, a signal is output to a signal output line 2120 through the amplification transistor 2008. After that, the supply of the power source potential to the power source line 2100 is stopped. In this manner, a signal is output.

In contrast to such a conventional example, according to one embodiment of the present invention, the number of transistors can be reduced to one. Hereinafter, a transistor, a configuration of a circuit, and a driving method of the circuit in one embodiment of the present invention are described.

The transistor 205 that amplitudes an electrical signal generated by the photodiode 204 needs to possess high mobility characteristics. In addition, in order to prevent an output of an unnecessary potential to the output signal line 212, it is preferable that the off-state current of the transistor 205 be small. Therefore, it is far preferable to use a transistor using an oxide semiconductor whose off-state current is extremely small as the transistor 205, than to use a transistor using a silicon semiconductor.

For example, as the oxide semiconductor, an oxide semiconductor represented by the chemical formula, $InMO_3(ZnO)_m$ (m>0), can be used, where M represents one or more metal elements selected from Ga, Al, Mn, and Co. For example, M is Ga, Ga and Al, Ga and Mn, Ga and Co, or the like.

The transistor 205 has a back gate, whose threshold voltage can be changed by changing the potential of the back gate. Such a transistor can be easily formed with a bottom-gate structure by forming an electrode as a back gate to cover a channel portion with an interlayer insulating film provided therebetween. Hereinafter, an example of using an n-channel transistor as the transistor 205, the absolute value of threshold voltage of which decreases as the potential of the back gate is increased and increases as the potential of the back gate is decreased.

Next, a precharge circuit is described below. In FIG. 1A, the precharge circuit 200 for one column of pixels includes a transistor 213 and a precharge signal line 214. An OP amplifier and/or an A/D converter may be connected to the precharge circuit 200.

In the precharge circuit 200, the potential of a photosensor signal line is set at a reference potential prior to the operation of the photosensor in the pixel. With the configuration of FIG. 1A, the potential of the precharge signal line 214 is set at "H (High)" to turn on the transistor 213, so that the voltage of the output signal line 212 can be set at a reference voltage (a high potential in this embodiment). It is effective to provide a storage capacitor for the output signal line 212 in order to stabilize the potential of the output signal line 212, though not shown. The reference potential may be a low potential.

Figure 1B:
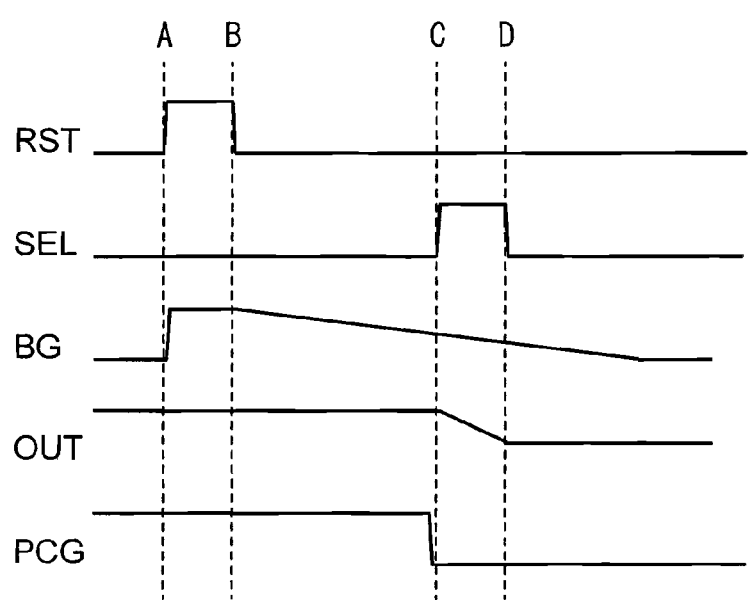
FIG. 1B is a timing chart thereof.

Next, a reading operation of the photosensor of this embodiment is described using a timing chart shown in FIG. 1B. In FIG. 1B, potential of the reset signal line 209 (RST), potential of the selection signal line 208 (SEL), potential of the back-gate signal line 206 (BG), potential of the output signal line 212 (OUT), and potential of the precharge signal line 214 (PCG) are shown sequentially from the top.

At time A, the potential (RST) of the reset signal line 209 is set at "H", so that the photodiode 204 is forward biased and the potential (BG) of the back-gate signal line 206 becomes a reset potential. This reset potential is lower than the "H" potential of the potential (RST) of the reset signal line 209 by a forward voltage (Vf) of the photodiode 204. This reset potential is retained in the signal charge accumulation portion formed by a parasitic capacitance of the back-gate signal line 206 and a capacitance of the back-gate portion of the transistor 205. This step is a beginning of a reset operation. The threshold voltage of the transistor 205 is lowered by a change of the threshold voltage, caused by application of the reset potential.

Further, at the time A, the potential (PCG) of the precharge signal line 214 is set at "H", so that the potential (OUT) of the output signal line 212 is precharged to "H"; this can be performed anytime before the transistor 205 is turned on, without being limited to the time A.

At time B, the potential (RST) of the reset signal line 209 is set at "L (Low)", so that a current of the photodiode 204 flows in the inverse direction in accordance with the light intensity, which lowers the potential (BG) of the back-gate signal line 206 from the reset potential. This step is an end of the reset operation and is a beginning of an accumulation operation. As a result, the potential (BG) of the back-gate signal line 206 is changed.

For example, operations in respective cases where the photodiode 204 is irradiated with light with illuminance A and light with illuminance B which is higher than the illuminance A are described below. When the photodiode 204 is irradiated with light with the illuminance A, a current of the photodiode 204 flows in the inverse direction, so that the potential (BG) of the back-gate signal line 206 is reduced to a certain level of potential from the reset potential in period T. On the other hand, when the photodiode 204 is irradiated with light with the illuminance B, larger current in the inverse direction than the case of the irradiation with the illuminance A flows through the photodiode 204, so that the potential (BG) of the back-gate signal line 206 is reduced to the certain level of potential from the reset potential in a period shorter than the period T. That is, the higher the illuminance of light with which the photodiode 204 is irradiated, the more the change of the potential (BG) of the back-gate signal line 206 in a certain period.

At that time, since the potential of the back gate of the transistor 205 is lower than the reset potential, the threshold voltage of the transistor 205 is increased.

Next, the potential (PCG) of the precharge signal line 214 is set at "L" to stop precharging the potential (OUT) of the output signal line 212. At time C, the potential (SEL) of the selection signal line 208 is set at "H" to turn on the transistor 205, so that the reference signal line 211 which is set at, for example, the ground potential, is electrically connected to the output signal line 212 via the transistor 205. This step is a beginning of a section operation. Since the threshold voltage is changed as described above before this step, a current flows through the transistor 205 in accordance with the electrical characteristics, lowering the potential (OUT) of the output signal line 212. The potential of the reference signal line 211 is not limited to the ground potential; an appropriate potential may be supplied thereto.

At time D, the potential (SEL) of the selection signal line 208 is set at "L" to turn off the transistor 205, so that the potential (OUT) of the output signal line 212 is retained. This step is end of the accumulation operation and the selection operation. The potential (OUT) of the output signal line 212 at that time is one which is changed depending on the intensity of light with which the photodiode 204 is irradiated during the accumulation operation. Therefore, the intensity of light with which the photodiode 204 is irradiated during the accumulation operation can be found by detecting the potential (OUT) of the output signal line 212.

The above-descried reset operation, accumulation operation, and selection operation are repeated per row of a pixel matrix in sequence, whereby an image can be picked up.

The above-described series of operations are an example in the case where the cathode of the photodiode 204 is connected on the back-gate side of the transistor 205. Such an operation of generating an output signal can also be performed with the case where the anode of the photodiode 204 is connected on the back-gate side of the transistor 205.

According to the above-described series of operations, the potential (BG) of the back-gate signal line 206 is initialized to "H" and discharged by a current in the inverse direction generated by light with which the photodiode 204 is irradiated, and an output signal is output through the transistor.

On the other hand, in the case where the photodiode 204 is connected inversely with respect to the photodiode 204 shown in FIG. 1A, the potential (BG) of the back-gate signal line 206 is initialized to "L" and charged by a current in the inverse direction occurred by light with which the photodiode 204 is irradiated, and an output signal can be output through the transistor.

In this manner, the photosensor according to this embodiment can consist of one photodiode, one transistor, and a variety of signal lines. The reduction in the number of transistors to one leads to reduction in area occupied by one photosensor portion, which enables high integration and increase in area of the display element and/or light reception area of the photodiode. The transistor may be formed using an oxide semiconductor, which enables formation of a circuit whose off-state current is extremely small, so that an image pick-up with a large dynamic range can be performed.

It is effective that the photosensor according to this embodiment is applied to a semiconductor device where photosensor portions are integrated in high density such as a CMOS image sensor.

Next, a structure in the case where the photosensor according to this embodiment is applied to a display device and used as a touch sensor or an image sensor is described below.

Figure 3:
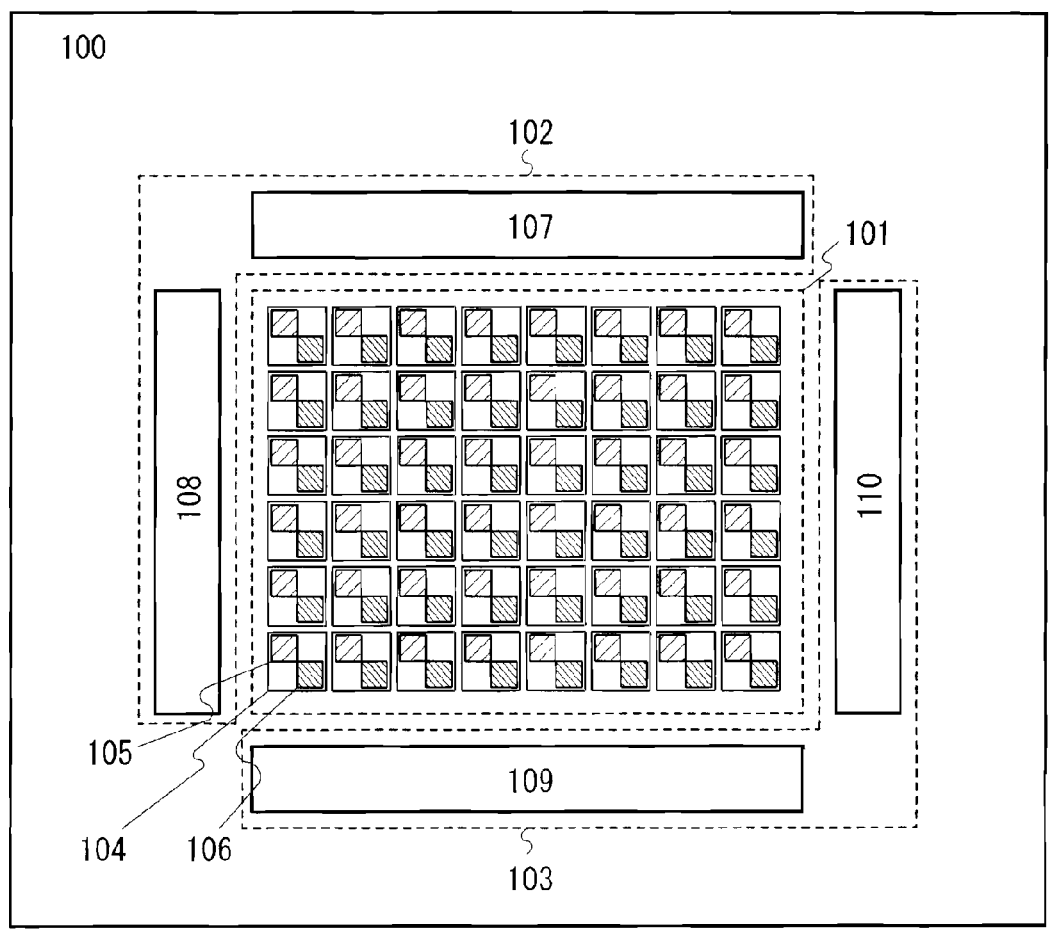
FIG. 3 is a diagram illustrating a structure of a semiconductor device in which a display element portion and a photosensor portion are provided in a display region.

FIG. 3 illustrates an example of a structure of the display device. A display device 100 includes a pixel circuit 101, a display element control circuit 102, and a photosensor control circuit 103. The pixel circuit 101 includes a plurality of pixels 104 arranged in a matrix of rows and columns. Each pixel 104 includes a display element portion 105 and a photosensor portion 106; however, the photosensor portion 106 is not necessarily provided for each and every pixel. Which pixel the photosensor portion 106 is provided for can be determined as appropriate.

The display element control circuit 102 shown in FIG. 3 controls the display element portions 105 and includes a display element driver circuit 107 and a display element driver circuit 108. The display element driver circuit 107 inputs signals to the display element portions 105 through source lines (such as video data signal lines), and the display element driver circuit 108 inputs signals to the display element portions 105 through gate signal lines (such as scanning lines).

For example, the display element driver circuit 108 selects a display element included in the pixel in a row. In addition, the display element driver circuit 107 supplies a predetermined potential to the display element included in the pixel in the selected row. In the display element whose gate signal line is applied with a high potential by the display element driver circuit 108, a transistor is turned on and a potential which is supplied to the source signal line by the display element driver circuit 107 is supplied.

The photosensor control circuit 103 controls the photosensor portions 106 and includes a photosensor readout circuit 109 on a signal line side for a photosensor output signal line, a photosensor reference signal line, or the like, and a photosensor driver circuit 110 on a scanning line side for a photodiode reset signal line, the gate signal line for selecting a row from which data is read out, or the like.

The photosensor driver circuit 110 performs the above-described reset operation, accumulation operation, and selection operation on the photosensor portion 106 included in the pixel in a row. Further, the photosensor readout circuit 109 extracts an output signal of the photosensor portion 106 included in the pixel in the selected row. The photosensor readout circuit 109 can have a system in which an output, which is an analog signal, of the photosensor is extracted as an analog signal to the outside of the display device by an OP amplifier; or a system in which the output is converted into a digital signal by an A/D converter and then extracted to the outside of the display device.

Figure 4:
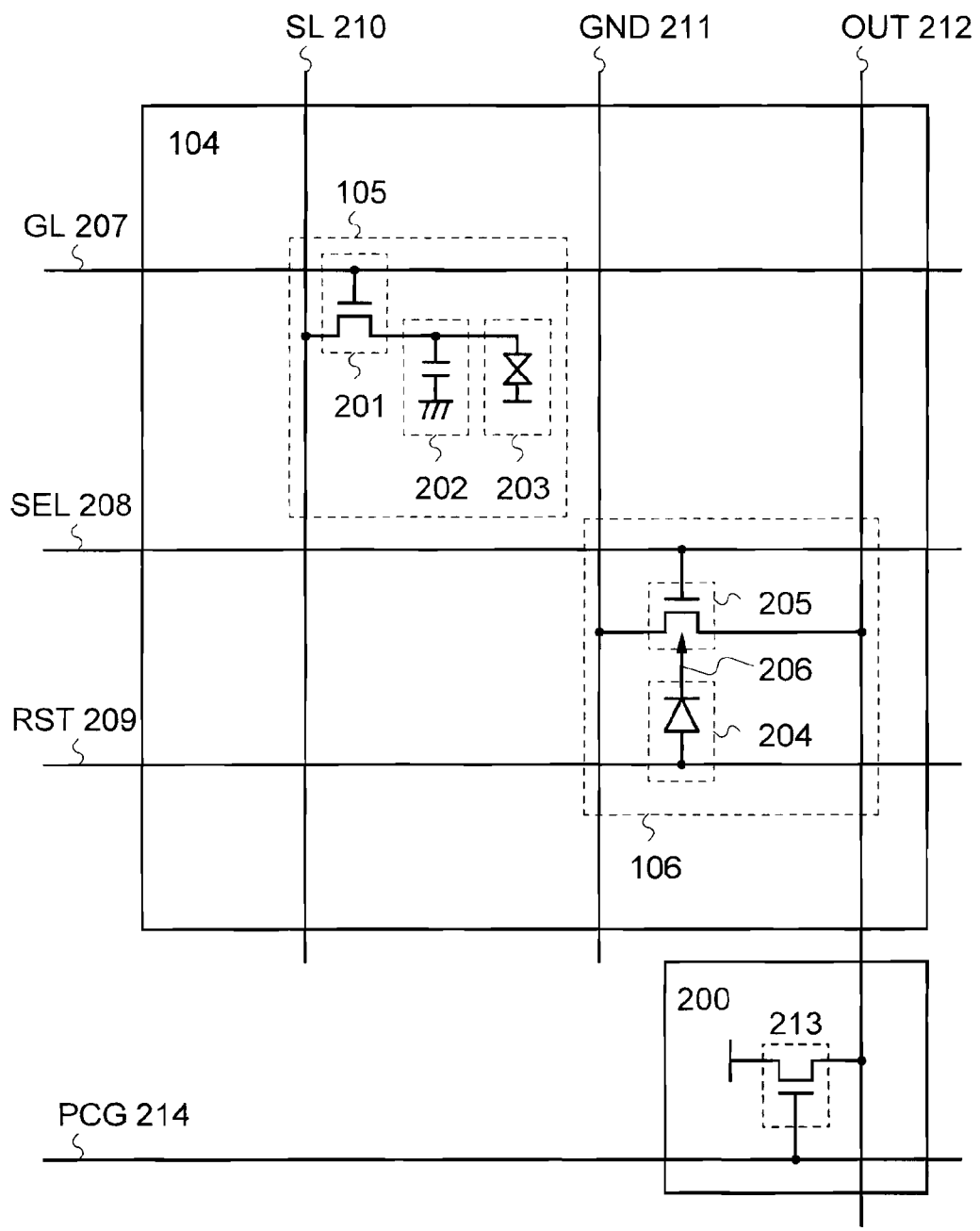
FIG. 4 is a diagram illustrating a configuration of a semiconductor device in which a display element portion and a photosensor portion are provided in a display region.

A circuit diagram of the pixel 104 is described using FIG. 4 below. The pixel 104 includes the display element portion 105 including a transistor 201, a storage capacitor 202, and a liquid crystal element 203, and the photosensor portion 106 including a photodiode 204 and a transistor 205.

In the display element portion 105, a gate of the transistor 201 is electrically connected to a gate signal line (GL) 207, one of a source and a drain of the transistor 201 is electrically connected to a source signal line (SL) 210, and the other of the source and the drain of the transistor 201 is electrically connected to one electrode of the storage capacitor 202 and one electrode of the liquid crystal element 203. The other electrode of the storage capacitor 202 and the other electrode of the liquid crystal element 203 are each held at a certain potential. The liquid crystal element 203 is an element including a pair of electrodes and a liquid crystal layer provided between the pair of electrodes.

The transistor 201 controls injection or ejection of electrical charge to/from the storage capacitor 202. For example, when a high potential is applied to the gate signal line (GL) 207, a potential of the source signal line (SL) 210 is supplied to the storage capacitor 202 and the liquid crystal element 203. The storage capacitor 202 retains electrical charge which corresponds to voltage applied to the liquid crystal element 203.

Gradation (gray levels) of light passing through the liquid crystal element 203 is/are formed using a change of the polarization direction caused by voltage application to the liquid crystal element 203, so that image display is performed. In a transmissive liquid crystal display device, a backlight may be used as a light source of the light passing through the liquid crystal element 203.

It is preferable that the transistor 201 be formed using an oxide semiconductor; however, an amorphous silicon semiconductor layer, a microcrystalline silicon semiconductor layer, a polycrystalline silicon semiconductor layer, or the like can be used as well. The off-state current of the transistor using an oxide semiconductor is extremely low, so that electrical charge storage properties can be increased.

Although the case where the display element portion 105 includes the liquid crystal element is described above, any other element such as a light emitting element may be included as well. The light emitting element, luminance of which is controlled by a current or a voltage, is a light emitting diode (LED), an organic light emitting diode (LED), or the like.

The above-described configuration can be applied to the photosensor portion 106 as it is. The precharge circuit 200 is included in the photosensor readout circuit 109.

In this manner, the photosensor according to this embodiment can be applied to a display device, so that the display device can be equipped with a function as a touch sensor or an image sensor. In addition, the number of transistors can be decreased to reduce the area of the photosensor portion, which can increase the area of the display element portion and improve the image quality of the display device.

Embodiment 1 can be implemented in combination with any of the other embodiments and examples as appropriate.
(Embodiment 2)

In Embodiment 2, a photosensor having a configuration different from Embodiment 1 will be described.

The photosensor in this embodiment further includes one transistor in the photosensor described in Embodiment 1. Therefore, Embodiment 1 can be referred to for the portion common to the photosensor described in Embodiment 1.

Figure 15:
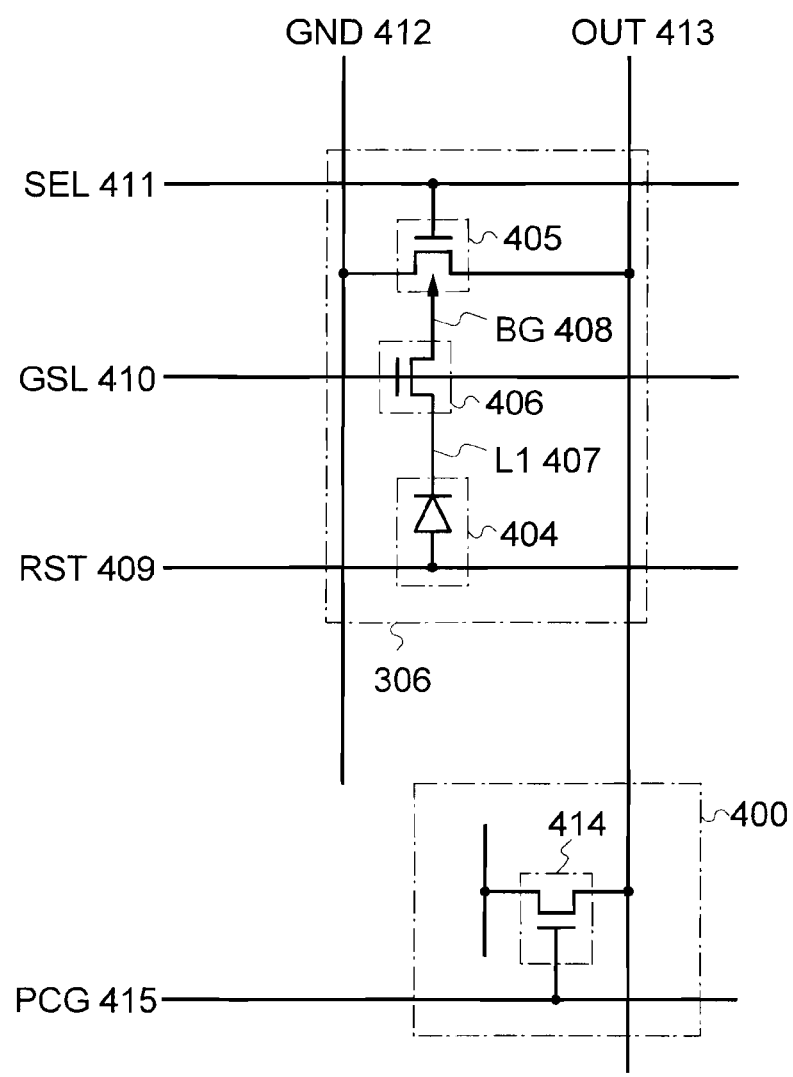
FIG. 15 is a diagram illustrating a configuration of a photosensor according to one embodiment of the present invention.

FIG. 15 illustrates a configuration for one pixel, of photosensors arranged in pixel matrix of a semiconductor device equipped with an image pick-up function, which includes a photodiode 404, a first transistor 405, and a second transistor 406.

An anode of the photodiode 404 is electrically connected to a photodiode reset signal line (hereinafter referred to as a reset signal line) 409, and a cathode thereof is electrically connected to a wiring 407. A gate of the first transistor 405, one of a source and a drain thereof, and the other of the source and the drain thereof are electrically connected to a gate signal line (hereinafter referred to as a selection signal line) 411, a photosensor output signal line (hereinafter referred to as an output signal line) 413, and a photosensor reference signal line (hereinafter referred to as a reference signal line) 412, respectively. A back gate of the first transistor 405 is electrically connected to a back-gate signal line 408. A gate of the second transistor 406, one of a source and a drain thereof, and the other of the source and the drain thereof are electrically connected to a gate signal line 410, the wiring 407, and the back-gate signal line 408, respectively.

In this embodiment, elements included in a photosensor portion 306 are two transistors and one photodiode, whereby the area of the photosensor portion can be extremely small, which makes it easy to integrate photosensors in high density. A precharge circuit 400, which is shown in FIG. 15 for clear explanation made later of an example of an operation, is not necessarily provided; resistive dividing or the like may be employed.

The first transistor 405 has the back gate, whose threshold voltage can be changed by changing the potential of the back gate. Such a transistor can be easily formed with a bottom-gate structure by forming an electrode as a back gate which covers a channel portion with an interlayer insulating film provided therebetween.

The first transistor 405 that amplitudes an electrical signal generated by the photodiode 404 needs to possess high mobility characteristics. In addition, in order to prevent an output of an unnecessary potential to the photosensor output signal line 413, it is preferable that the off-state current of the transistor be small.

It is necessary that the field-effect mobility of the second transistor 406, which accumulates an output signal of the photodiode 404 as electrical charge in the back gate of the first transistor 405 and retains the electrical charge, be high and the off-state current thereof be extremely small.

In order to form such a transistor, it is preferable that a semiconductor layer be formed using an oxide semiconductor. Embodiment 1 can be referred to for the specific description on the oxide semiconductor.

In FIG. 15, the precharge circuit 400 for one column of photosensors includes a transistor 414 and a precharge signal line 415 is connected to a gate of the transistor 414. An OP amplifier and/or an A/D converter may be connected to the precharge circuit 400. Embodiment 1 can be referred to for the specific description on the precharge circuit.

Next, an operation of the photosensor portion 306 is described below using timing charts shown in FIGS. 16A and 16B.

Figure 16A:
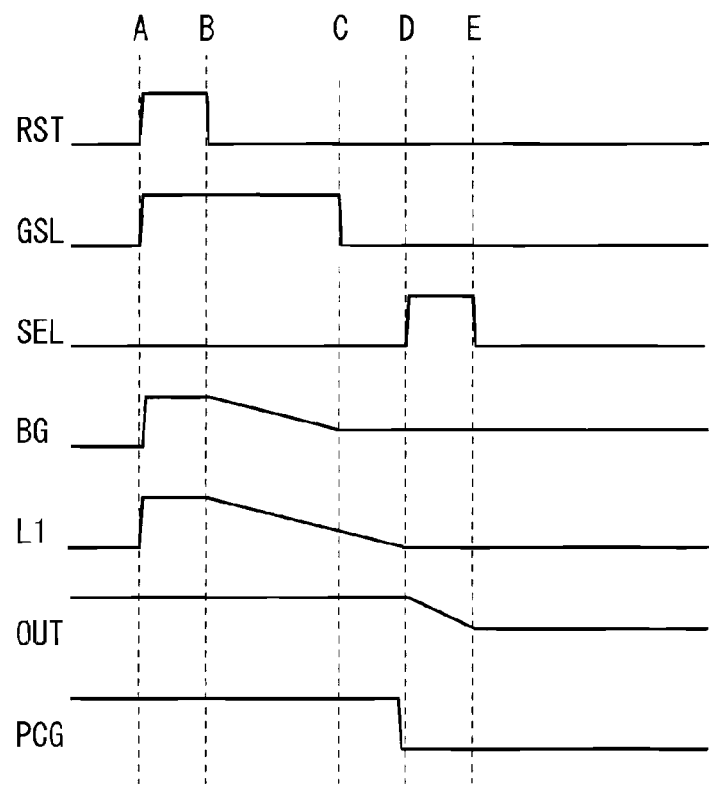
FIGS. 16A and 16B are timing charts illustrating operations of a photosensor according to one embodiment of the present invention.
Figure 16B:
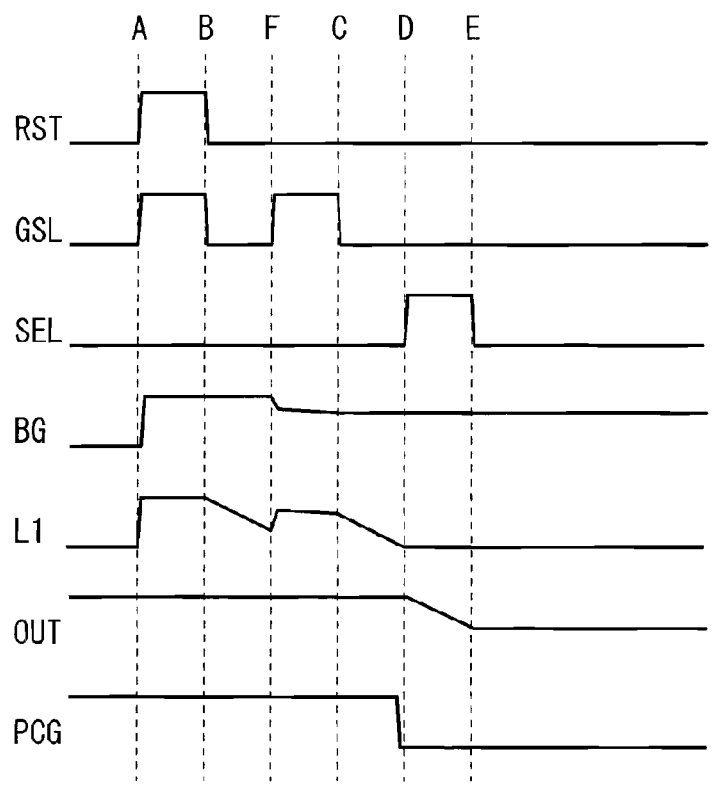

A reading operation of the photosensor of this embodiment is described using the timing chart shown in FIG. 16A. In FIG. 16A, potential of the reset signal line 409 (RST), potential of the gate signal line 410 (GSL), potential of the selection signal line 411 (SEL), potential of the back-gate signal line 408 (BG), potential of the wiring 407 (L1), potential of the output signal line 413 (OUT), and potential of the precharge signal line 415 (PCG) are shown sequentially from the top.

At time A, the potential (RST) of the reset signal line 409 is set at "H" and the potential (GSL) of the gate signal line 410 is set at "H" (a reset operation starts), so that the photodiode 404 is forward biased and the second transistor 406 is turned on, which makes the potential (L1) of the wiring 407 "H" with the photodiode 404 and makes the potential (BG) of the back-gate signal line 408 "H" with the photodiode 404 and the second transistor 406. Further, the potential (PCG) of the precharge signal line 415 may be set at "H" to turn the transistor 414 on, so that the potential (OUT) of the output signal line 413 is precharged to "H".

At time B, the potential (RST) of the reset signal line 409 is set at "L (Low)" and the potential (GSL) of the gate signal line 410 is kept at "H" (the reset operation ends and an accumulation operation starts), so that a current of the photodiode 404 flows in the inverse direction in accordance with the light intensity, which lowers the potential (BG) of the back-gate signal line 408 and the potential (L1) of the wiring 407. At this step, as the potential of the back gate of the first transistor 405 changes, the threshold voltage thereof is changed.

At time C, the potential (GSL) of the gate signal line 410 is set at "L" to turn off the second transistor 406 (the accumulation operation ends), so that the change of the potential (BG) of the back-gate signal line 408 is stopped at a certain potential which is determined depending on the amount of the electrical charge supplied by the photodiode 404 during the accumulation operation, i.e., the intensity of light with which the photodiode 404 is irradiated. Since the second transistor 406 is a transistor which includes an oxide semiconductor layer and whose off-state current is extremely small, the above-described amount of electrical charge can be retained until a selection operation is performed later.

When the potential (GSL) of the gate signal line 410 is set at "L", the parasitic capacitance between the gate signal line 410 and the back-gate signal line 408 causes change the potential of the back-gate signal line 408, that is, the potential of the back gate. If the amount of change of the potential is large, the amount of electrical charge supplied by the photodiode 404 during the accumulation operation cannot be detected precisely. As a countermeasure to reduce the amount of change of the potential, the following is effective: reduction of the gate-source (or gate-drain) capacitance of the second transistor 406, increase of the gate capacitance on the back-gate side of the first transistor 405, provision of a storage capacitor for the back-gate signal line 408, or the like. In FIG. 16A, such a countermeasure is already taken, so that the above-described potential change can be ignored.

Then, prior to time D, the potential (PCG) of the precharge signal line 415 is set at "L" to end the precharge of the output signal line 413. At the time D, the potential (SEL) of the selection signal line 411 is set at "H" (a selection operation starts) to turn on the first transistor 405, which electrically connects the reference signal line 412 to the output signal line 413. Consequently, the potential (OUT) of the output signal line 413 starts lowering.

The rate at which the potential (OUT) of the output signal line 413 lowers depends on the source-drain current of the first transistor 405. That is, the potential (OUT) of the output signal line 413 is determined depending on the intensity of light with which the photodiode 404 is irradiated during the accumulation operation.

Specifically, the stronger the light with which the photodiode 404 is irradiated, the lower the potential of the back-gate signal line 408 and the higher the threshold voltage of the first transistor 405, so that the source-drain resistance of the first transistor 405 in the on state is increased, which slows down the rate at which the potential (OUT) of the output signal line 413 lowers; accordingly, the stronger the light with which the photodiode 404 is irradiated, the higher the potential (OUT) of the output signal line 413. To the contrary, the weaker the light with which the photodiode 404 is irradiated, the lower the potential (OUT) of the output signal line 413.

At time E, the potential (SEL) of the selection signal line 411 is set at "L" (the selection operation ends) to turn off the first transistor 405, so that the potential (OUT) of the output signal line 413 is stopped lowering at a certain potential. The certain potential is determined in accordance with the intensity of light with which the photodiode 404 is irradiated. Therefore, the intensity of light with which the photodiode 404 is irradiated during the accumulation operation can be found by detecting the potential (OUT) of the output signal line 413.

Next, a series of operations which are different from the series of operations described using the timing chart shown in FIG. 16A are described using the timing chart shown in FIG. 16B below.

At time A, the potential (RST) of the reset signal line 409 is set at "H" and the potential (GSL) of the gate signal line 410 is set at "H" (a reset operation starts), so that the photodiode 404 is forward biased and the second transistor 406 is turned on, which makes the potential (L1) of the wiring 407 "H" with the photodiode 404 and makes the potential (BG) of the back-gate signal line 408 "H" with the photodiode 404 and the second transistor 406. Further, the potential (PCG) of the precharge signal line 415 may be set at "H" to turn the transistor 414 on, so that the potential (OUT) of the output signal line 413 is precharged to "H".

At time B, the potential (RST) of the reset signal line 409 is set at "L" and the potential (GSL) of the gate signal line 410 is set at "L" to turn off the second transistor 406 (the reset operation ends and an accumulation operation starts), so that a current of the photodiode 404 flows in the inverse direction in accordance with the light intensity, which lowers the potential (L1) of the wiring 407. The photodiode 404, which increases the current in the inverse direction when being irradiated with light, changes the potential (L1) of the wiring 407 in accordance which light with which the photodiode 404 is irradiated; the potential (BG) of the back-gate signal line 408 does not change.

At time F, the potential (GSL) of the gate signal line 410 is set at "H" to turn on the second transistor 406, which electrically connects the back-gate signal line 408 to the wiring 407. Accordingly, the potential (BG) of the back-gate signal line 408 becomes equal to the potential (L1) of the wiring 407. The potential (BG) of the back-gate signal line 408 and the potential (L1) of the wiring 407 are changed depending on the intensity of light with which the photodiode 404 is irradiated. In this manner, the potential of the back gate of the first transistor 405 changes, so that the threshold voltage thereof is changed.

At time C, the potential (GSL) of the gate signal line 410 is set at "L" to turn off the second transistor 406 (the accumulation operation ends), so that the change of the potential (BG) of the back-gate signal line 408 is stopped at a certain potential which is determined depending on the electrical charge supplied by the photodiode 404 during the accumulation operation, i.e., the intensity of light with which the photodiode 404 is irradiated. Since the second transistor 406 is a transistor which includes an oxide semiconductor layer and whose off-state current is extremely small, the above-described amount of electrical charge can be retained until a selection operation is performed later.

When the potential (GSL) of the gate signal line 410 is set at "L", the parasitic capacitance between the gate signal line 410 and the back-gate signal line 408 causes change the potential of the back-gate signal line 408, that is, the potential of the back gate. If the amount of change of the potential is large, the amount of electrical charge supplied by the photodiode 404 during the accumulation operation cannot be detected precisely. As a countermeasure to reduce the amount of change of the potential, the following is effective: reduction of the gate-source (or gate-drain) capacitance of the second transistor 406, increase of the gate capacitance on the back-gate side of the first transistor 405, provision of a storage capacitor for the back-gate signal line 408, or the like. In FIG. 16B, such a countermeasure is already taken, so that the above-described potential change can be ignored.

Then, prior to time D, the potential (PCG) of the precharge signal line 415 is set at "L" to end the precharge of the output signal line 413. At the time D, the potential (SEL) of the selection signal line 411 is set at "H" (a selection operation starts) to turn on the first transistor 405, which electrically connects the reference signal line 412 to the output signal line 413. Consequently, the potential (OUT) of the output signal line 413 starts lowering.

The rate at which the potential (OUT) of the output signal line 413 lowers depends on the source-drain current of the first transistor 405. That is, the potential (OUT) of the output signal line 413 is determined depending on the intensity of light with which the photodiode 404 is irradiated during the accumulation operation.

Specifically, the stronger the light with which the photodiode 404 is irradiated, the lower the potential of the back-gate signal line 408 and the higher the threshold voltage of the first transistor 405, so that the source-drain resistance of the first transistor 405 in the on state is increased, which slows down the rate at which the potential (OUT) of the output signal line 413 lowers; accordingly, the stronger the light with which the photodiode 404 is irradiated, the higher the potential (OUT) of the output signal line 413. To the contrary, the weaker the light with which the photodiode 404 is irradiated, the lower the potential (OUT) of the output signal line 413.

At time E, the potential (SEL) of the selection signal line 411 is set at "L" (the selection operation ends) to turn off the first transistor 405, so that the potential (OUT) of the output signal line 413 is stopped lowering at a certain potential. The certain potential is determined in accordance with the intensity of light with which the photodiode 404 is irradiated. Therefore, the intensity of light with which the photodiode 404 is irradiated during the accumulation operation can be found by detecting the potential (OUT) of the output signal line 413.

In this manner, each photosensor is operated by repeating the series of operations including a reset operation, an accumulation operation, and a selection operation. The above-descried reset operation, accumulation operation, and selection operation are repeated per row of a pixel matrix, whereby an image can be picked up.

The above-described series of operations are an example in the case where the cathode of the photodiode 404 is connected to the second transistor 406. Such an operation of generating an output signal can also be performed with the case where the anode of the photodiode 404 is connected on the second transistor 406 side.

According to the above-described series of operations, the potential (BG) of the back-gate signal line 408 is initialized to "H" and discharged by a current in the inverse direction occurred by light with which the photodiode 404 is irradiated, and an output signal is output through the transistor.

On the other hand, in the case the photodiode 404 is connected in the inverse direction to the connection direction of the photodiode 404 shown in FIG. 15, the potential (BG) of the back-gate signal line 408 is initialized to "L" and charged by a current in the inverse direction occurred by light with which the photodiode 404 is irradiated, and an output signal can be output through the transistor.

In this manner, the photosensor according to this embodiment can consist of one photodiode, two transistors, and a variety of signal lines. The reduction in the number of transistors leads to reduction in area occupied by one photosensor portion, which enables high integration and increase in area of the display element and/or area of the photodiode. The transistor may be formed using an oxide semiconductor, which enables formation of a circuit whose off-state current is extremely small, so that an image pick-up with a large dynamic range can be performed.

It is effective that the photosensor according to this embodiment is applied to a semiconductor device where photosensor portions are integrated in high density such as a CMOS image sensor.

Embodiment 1 can be referred to for a structure in the case where the photosensor according to this embodiment is applied to a display device and used as a touch sensor or an image sensor.

Embodiment 2 can be implemented in combination with any of the other embodiments and examples as appropriate.

(Embodiment 3)

In Embodiment 3, an example of a transistor which can be applied to a semiconductor device disclosed in this specification will be described.

There is no particular limitation on a structure of a transistor which can be applied to the semiconductor device disclosed in this specification: for example, a top-gate structure or a bottom-gate structure such as a staggered type and a planar type can be used. Further, the transistor may have a single gate structure including one channel formation region, a double gate structure including two channel formation regions, or a triple gate structure including three channel formation regions.

Figure 5A:
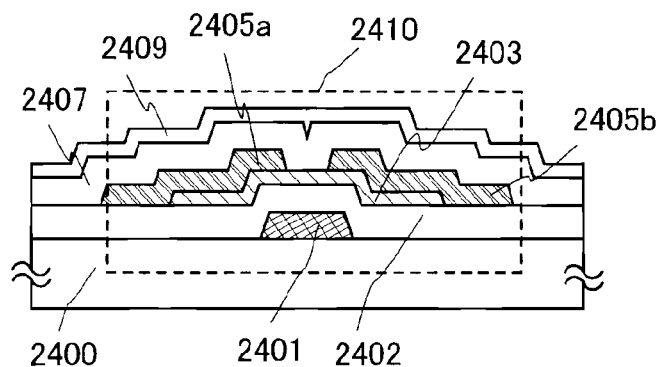
FIGS. 5A to 5D are cross-sectional views illustrating structures of transistors.

Examples of a cross-sectional structure of the transistor shown in FIGS. 5A to 5D are described below. One embodiment of the present invention features in that as a back-gate electrode a conductive layer which is formed so as to face a gate electrode of the transistor with a gate insulating film, a semiconductor layer serving as a channel formation region, and an insulating film provided therebetween is used. A transistor shown in FIG. 5A provided with a back gate is shown in FIG. 5A as an example; a back gate may be provided for any of transistors shown in FIGS. 5B to 5D so as to face a gate electrode in a similar manner.

The transistors shown in FIGS. 5A to 5D are formed using an oxide semiconductor. An advantage of using an oxide semiconductor lies in high mobility and low off-state current; however, any other semiconductor may be used as well.

A transistor 2410 shown in FIG. 5A is one of bottom-gate transistors and is also called an inverted staggered transistor.

The transistor 2410 includes, over a substrate 2400 having an insulating surface, a gate electrode layer 2401, a gate insulating layer 2402, an oxide semiconductor layer 2403, a source electrode layer 2405a, and a drain electrode layer 2405b, and an insulating layer 2407 and a protective insulating layer 2409 which cover them.

Figure 14:
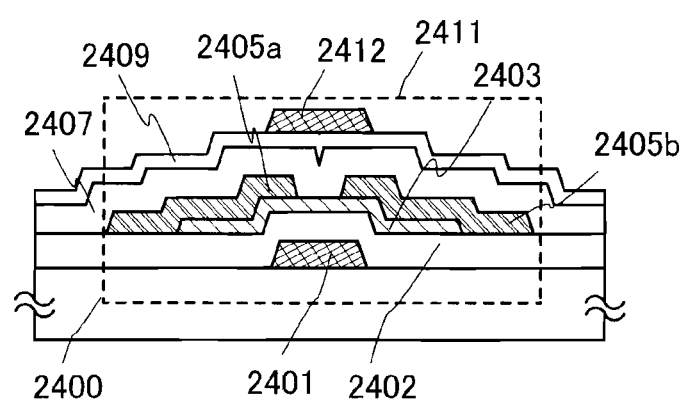
FIG. 14 is a cross-sectional view illustrating a structure of a transistor.

In the case where a back gate is provided, as shown in FIG. 14, a conductive layer 2412 used as the back gate may be formed over an insulating layer 2407 or a protective insulating layer 2409 so as to overlap with a channel formation region. The same can be applied to the other structures below except the top-gate structure.

Figure 5B:
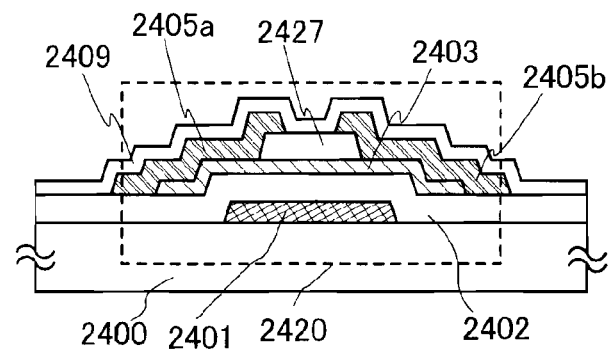

A transistor 2420 shown in FIG. 5B is a kind of bottom-gate structure referred to as a channel-protective type and is also called an inverted staggered transistor.

The transistor 2420 includes, over a substrate 2400 having an insulating surface, a gate electrode layer 2401, a gate insulating layer 2402, an oxide semiconductor layer 2403, an insulating layer 2427 serving as a channel protective layer which covers a channel formation region of the oxide semiconductor layer 2403, a source electrode layer 2405a, and a drain electrode layer 2405b, and a protective insulating layer 2409 which covers them.

Figure 5C:
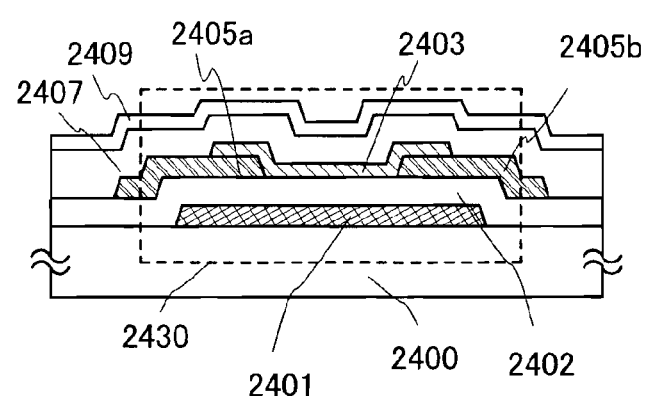

A transistor 2430 shown in FIG. 5C is a bottom-gate transistor, and includes, over a substrate 2400 having an insulating surface, a gate electrode layer 2401, a gate insulating layer 2402, an oxide semiconductor layer 2403, a source electrode layer 2405a, a drain electrode layer 2405b, and an oxide semiconductor layer 2403, and an insulating layer 2407 and a protective insulating layer 2409 which cover them.

In the transistor 2430, the gate insulating layer 2402 is provided on and in contact with the substrate 2400 and the gate electrode layer 2401; the source electrode layer 2405a and the drain electrode layer 2405b are provided on and in contact with the gate insulating layer 2402. Further, the oxide semiconductor layer 2403 is provided over the gate insulating layer 2402, the source electrode layer 2405a, and the drain electrode layer 2405b.

Figure 5D:
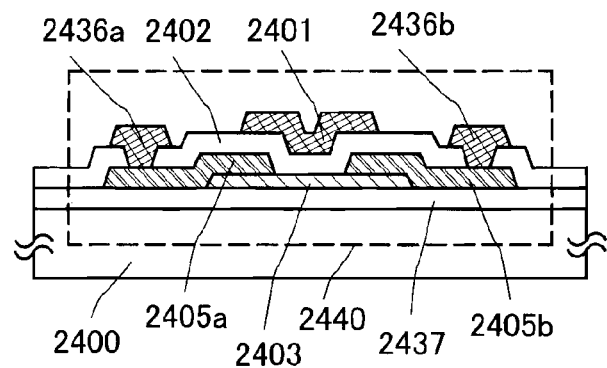

A transistor 2440 shown in FIG. 5D is one of top-gate transistors. The transistor 2440 includes, over a substrate 2400 having an insulating surface, an insulating layer 2437, an oxide semiconductor layer 2403, a source electrode layer 2405a, a drain electrode layer 2405b, a gate insulating layer 2402, and a gate electrode layer 2401. A wiring layer 2436a and a wiring layer 2436b are provided in contact with and electrically connected to the source electrode layer 2405a and the drain electrode layer 2405b, respectively. In the case where a back gate is provided for this structure, a conductive layer and an insulating layer may be formed so as to overlap with a channel formation region before the formation of the oxide semiconductor layer 2403.

In this embodiment, as described above, the oxide semiconductor layer 2403 is used as a semiconductor layer included in the transistor. The oxide semiconductor layer 2403 can be formed using the following oxide semiconductor material: In—Sn—Ga—Zn—O-based metal oxide which is four-component metal oxide; In—Ga—Zn—O-based metal oxide, In—Sn—Zn—O-based metal oxide, In—Al—Zn—O-based metal oxide, Sn—Ga—Zn—O-based metal oxide, Al—Ga—Zn—O-based metal oxide, or Sn—Al—Zn—O-based metal oxide which are three-component metal oxide; In—Zn—O-based metal oxide, Sn—Zn—O-based metal oxide, Al—Zn—O-based metal oxide, Zn—Mg—O-based metal oxide, Sn—Mg—O-based metal oxide, or In—Mg—O-based metal oxide which are two-component metal oxide; or In—O-based metal oxide, Sn—O-based metal oxide, Zn—O-based metal oxide, or the like. Further, Si may be contained in the oxide semiconductor. In this embodiment, for example, the In—Ga—Zn—O-based oxide semiconductor is an oxide semiconductor including at least In, Ga, and Zn, and there is no particular limitation on the composition ratio thereof. Further, the In—Ga—Zn—O-based oxide semiconductor may contain an element other than In, Ga, and Zn.

A thin film represented by the chemical formula, $InMO_3(ZnO)_m$ (m>0) can be used as the oxide semiconductor layer 2403, where, M represents one or more metal elements selected from Ga, Al, Mn, and Co. For example, M can be Ga, Ga and Al, Ga and Mn, Ga and Co, or the like.

With the oxide semiconductor layer 2403 used in the transistors 2410, 2420, 2430, and 2440, the current value in an off state (off-state current value) can be reduced. Accordingly, the retention time of electrical signals such as video image data can be prolonged, which results in reduction of power consumption.

Further, with the oxide semiconductor layer 2403 used in the transistors 2410, 2420, 2430, and 2440, relatively high field-effect mobility can be obtained, which enables high-speed operation. Accordingly, for example, in a display device or the like, a driver circuit portion can be manufactured over the same substrate as a pixel portion, which leads to reduction of the number of components.

As the substrate 2400 having an insulating surface, a glass substrate formed using barium borosilicate glass, alumino-borosilicate glass, or the like can be used.

In the bottom-gate transistors 2410, 2420, and 2430, an insulating film serving as a base film may be provided between the substrate and the gate electrode layer. The base film prevents diffusion of an impurity element from the substrate, and can be formed to have a single-layer structure or a stacked-layer structure using one or more films selected from a silicon nitride film, a silicon oxide film, a silicon nitride oxide film, and a silicon oxynitride film.

The gate electrode layer 2401 can be formed using a metal material such as molybdenum, titanium, chromium, tantalum, tungsten, aluminum, copper, neodymium, or scandium or an alloy material which contains any of these materials as its main component. Further, the gate electrode layer 2401 is not limited to a single layer: a stacked layer including films different from each other may be employed as the gate electrode layer 2401.

The gate insulating layer 2402 can be formed using a silicon oxide layer, a silicon nitride layer, a silicon oxynitride layer, a silicon nitride oxide layer, an aluminum oxide layer, an aluminum nitride layer, an aluminum oxynitride layer, an aluminum nitride oxide layer, or a hafnium oxide layer by a plasma CVD method, a sputtering method, or the like. Further, the gate insulating layer 2402 is not limited to a single layer: a stacked layer including films different from each other may be employed as the gate insulating layer 2402. For example, a silicon nitride layer ($SiN_y$ (y>0)) with a thickness greater than or equal to 50 nm and less than or equal to 200 nm is formed as a first gate insulating layer by a plasma CVD method, and a silicon oxide layer ($SiO_x$ (x>0)) with a thickness greater than or equal to 5 nm and less than or equal to 200 nm is formed as a second gate insulating layer over the first gate insulating layer, so that a gate insulating layer with a thickness of 200 nm in total is formed.

A conductive film used as the source electrode layer 2405a and the drain electrode layer 2405b can be formed using an element selected from Al, Cr, Cu, Ta, Ti, Mo, and W, an alloy containing any of these elements, or the like. Alternatively, a structure may be employed in which a high-melting-point metal layer of Ti, Mo, W, or the like is stacked over and/or below a metal layer of Al, Cu, or the like. Heat resistance can be improved by using an Al material to which an element (Si, Nd, Sc, or the like) which prevents generation of a hillock or a whisker in an Al film is added.

The conductive film such as the wiring layer 2436a and the wiring layer 2436b which are connected to the source electrode layer 2405a and the drain electrode layer 2405b, respectively can be formed using a material similar to that of the source electrode layer 2405a and the drain electrode layer 2405b.

The conductive film to be the source electrode layer 2405a and the drain electrode layer 2405b (including a wiring layer formed of the same layer as the source electrode layer 2405a and the drain electrode layer 2405b) may be formed using conductive metal oxide. As the conductive metal oxide, indium oxide ($In_2O_3$), tin oxide ($SnO_2$), zinc oxide (ZnO), indium oxide-tin oxide alloy ($In_2O_3$—$SnO_2$, which is abbreviated to ITO), indium oxide-zinc oxide alloy ($In_2O_3$—ZnO), or any of these metal oxide materials in which silicon is contained can be used.

As the insulating layers 2407, 2427, and 2437, typically, an inorganic insulating film such as a silicon oxide film, a silicon oxynitride film, an aluminum oxide film, or an aluminum oxynitride film can be used.

For the protective insulating layer 2409, an inorganic insulating film such as a silicon nitride film, an aluminum nitride film, a silicon nitride oxide film, or an aluminum nitride oxide film can be used.

Further, a planarization insulating film may be formed over the protective insulating layer 2409 in order to reduce the surface roughness due to the structure of the transistor. As the planarization insulating film, an organic material such as polyimide, acrylic, or benzocyclobutene can be used. Other than such an organic material, it is also possible to use a low-dielectric constant material (a low-k material) or the like. A plurality of insulating films formed using these materials may be stacked to form the planarization insulating film.

In this manner, a high-functional semiconductor device can be provided by using a transistor including an oxide semiconductor layer in this embodiment.

Embodiment 3 can be implemented in combination with any of the other embodiments and examples as appropriate.

(Embodiment 4)

In Embodiment 4, an example of a transistor including an oxide semiconductor layer in one embodiment of the present invention and an example of a manufacturing method thereof will be described in detail using drawings.

FIGS. 6A to 6E illustrate an example of a cross-sectional structure of a transistor. A transistor 2510 shown in FIGS. 6A to 6E is an inverted staggered transistor having a bottom-gate structure, which is similar to the transistor 2410 shown in FIG. 5A.

An oxide semiconductor used for a semiconductor layer in this embodiment is an i-type (intrinsic) oxide semiconductor or a substantially i-type (intrinsic) oxide semiconductor, which is obtained in such a manner that hydrogen, which forms a donor, is removed from an oxide semiconductor as much as possible to highly purify and the oxide semiconductor so as to contain as few impurities that are not main components of the oxide semiconductor as possible. In other words, this embodiment features that a purified i-type (intrinsic) semiconductor, or a semiconductor close thereto, is obtained not by adding an impurity but by removing an impurity such as hydrogen or water as much as possible. Accordingly, the oxide semiconductor layer included in the transistor 2510 is an oxide semiconductor layer which is highly purified and made to be electrically i-type (intrinsic).

In addition, the highly purified oxide semiconductor includes extremely few carriers (close to zero); the carrier concentration thereof is lower than $1\times10^{14}/cm^3$, preferably lower than $1\times10^{12}/cm^3$, far preferably lower than $1\times10^{11}/cm^3$.

Since the oxide semiconductor includes extremely few carriers, the off-state current of the transistor can be reduced. The smaller the off-state current is, the better.

Specifically, in the transistor including the above-described oxide semiconductor layer, the off-state current density per micrometer in channel width at room temperature can be reduced to less than or equal to 10 aA/μm ($1\times10^{-17}$ A/μm), further reduced to less than or equal to 1 aA/μm ($1\times10^{-18}$ A/μm), or still further reduced to less than or equal to 10 zA/μm ($1\times10^{-20}$ A/μm).

Moreover, the transistor 2510 including the oxide semiconductor layer exhibits little temperature dependence of on-state current, and fluctuation of the off-state current is extremely small.

A process of manufacturing the transistor 2510 over a substrate 2505 will be described below using FIGS. 6A to 6E.

First, a conductive film is formed over the substrate 2505 having an insulating surface, and then subjected to a first photolithography step and an etching step to form a gate electrode layer 2511. A resist mask may be formed by an inkjet method. Formation of the resist mask by an inkjet method needs no photomask; thus, manufacturing costs can be reduced.

As the substrate 2505 having an insulating surface, a substrate similar to the substrate 2400 described in Embodiment 3 can be used. In this embodiment, a glass substrate is used as the substrate 2505.

An insulating film serving as a base film may be provided between the substrate 2505 and the gate electrode layer 2511. The base film prevents diffusion of an impurity element from the substrate 2505, and can be formed to have a single-layer structure or a stacked-layer structure using one or more of a silicon nitride film, a silicon oxide film, a silicon nitride oxide film, and a silicon oxynitride film.

The gate electrode layer 2511 can be formed using a metal material such as molybdenum, titanium, tantalum, tungsten, aluminum, copper, neodymium, or scandium, or an alloy material which contains any of these materials as its main component. Further, the gate electrode layer 2511 is not limited to a single layer: a stacked layer including films different from each other may be employed as the gate electrode layer 2511.

Next, a gate insulating layer 2507 is formed over the gate electrode layer 2511. The gate insulating layer 2507 can be formed using a silicon oxide layer, a silicon nitride layer, a silicon oxynitride layer, a silicon nitride oxide layer, an aluminum oxide layer, an aluminum nitride layer, an aluminum oxynitride layer, an aluminum nitride oxide layer, or a hafnium oxide layer by a plasma CVD method, a sputtering method, or the like. Further, the gate insulating layer 2507 is not limited to a single layer: a stacked layer including films different from each other may be employed as the gate insulating layer 2507.

As the oxide semiconductor in this embodiment, an oxide semiconductor which is made to be an i-type or substantially i-type by removing impurities is used. Such a highly purified oxide semiconductor is highly sensitive to an interface state and interface charge; thus, an interface between the oxide semiconductor layer and the gate insulating layer is important. For that reason, the gate insulating layer that is to be in contact with a highly-purified oxide semiconductor needs to have high quality.

For example, high-density plasma CVD using microwaves (for example with a frequency of 2.45 GHz) is preferable because a dense high-quality insulating layer having high withstand voltage can be formed. Accordingly, the highly-purified oxide semiconductor can be in close contact with the high-quality gate insulating layer, whereby the interface state density can be reduced and high interface characteristics can be provided.

Needless to say, any other deposition method such as a sputtering method or a plasma CVD method can be used as long as a high-quality insulating layer can be formed as the gate insulating layer. Further, an insulating layer whose film quality and characteristic in the interface between the insulating layer and the oxide semiconductor are improved by heat treatment which is performed after formation of the insulating layer may be used as the gate insulating layer. In any case, any insulating layer can be used as long as the insulating layer has characteristics of enabling reduction in interface state density of the interface between the insulating layer and the oxide semiconductor and formation of a favorable interface as well as having high film quality as a gate insulating layer. In this embodiment, an example in which a sputtering method is used is described.

In order not to contain hydrogen, a hydroxyl group, and moisture in the gate insulating layer 2507, the oxide semiconductor film 2530 as much as possible, it is preferable to heat the substrate 2505 provided with the gate electrode layer 2511 or the substrate 2505 provided with the elements up to and including the gate insulating layer 2507 in a preheating chamber in a sputtering apparatus to detach and exhaust impurities such as hydrogen and moisture adsorbed to the substrate 2505, as a pretreatment of film deposition of the oxide semiconductor film 2530. As an exhaustion unit provided in the preheating chamber, a cryopump is preferable. This preheating treatment can be omitted. This preheating treatment may be performed on the substrate 2505 provided with the elements up to and including a source electrode layer 2515a and a drain electrode layer 2515b before the formation of an insulating layer 2516.

Figure 6A:
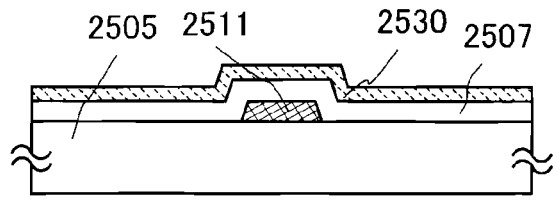
FIGS. 6A to 6E are cross-sectional views illustrating a method for manufacturing a transistor.
Figure 6B:
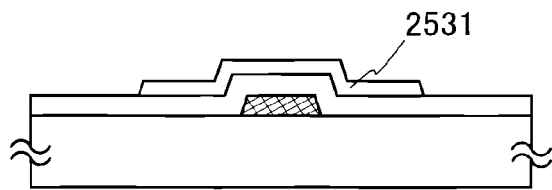
Figure 6C:
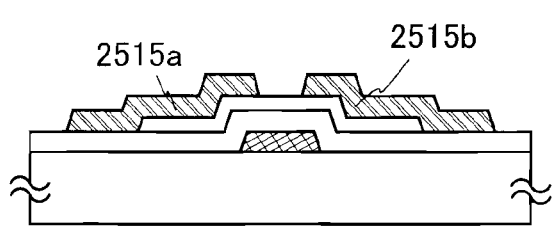

Next, over the gate insulating layer 2507, the oxide semiconductor film 2530 having a thickness greater than or equal to 2 nm and less than or equal to 200 nm, preferably greater than or equal to 5 nm and less than or equal to 30 nm is formed (see FIG. 6A).

Before the oxide semiconductor film 2530 is formed by a sputtering method, powdery substances (also referred to as particles or dust) which are attached to a surface of the gate insulating layer 2507 are preferably removed by reverse sputtering in which an argon gas is introduced and plasma is generated. According to the reverse sputtering, an RF power source is used for application of voltage to a substrate side in an argon atmosphere so that ionized argon collides with the substrate to modify a surface. Instead of an argon atmosphere, a nitrogen atmosphere, a helium atmosphere, an oxygen atmosphere, or the like may be used.

The oxide semiconductor film 2530 can be formed the following oxide semiconductor described in Embodiment 3: the four-compound metal oxide; the three-compound metal oxide; the two-compound metal oxide; an In—O-based metal oxide; a Sn—O-based metal oxide; a Zn—O-based metal oxide; or the like. Further, Si may be contained in the oxide semiconductor. In this embodiment, the oxide semiconductor film 2530 is formed by a sputtering method using an In—Ga—Zn—O-based metal oxide target. A cross-sectional view at this stage corresponds to FIG. 6A. The oxide semiconductor film 2530 can be formed by a sputtering method in a rare gas (typically, argon) atmosphere, an oxygen atmosphere, or a mixed atmosphere of a rare gas and oxygen.

The target for forming the oxide semiconductor film 2530 by a sputtering method is, for example, a metal oxide containing $In_2O_3$, $Ga_2O_3$, and ZnO with a composition ratio (molar ratio) of 1:1:1. Alternatively, metal oxide with the following composition ratio (molar ratio) may be used: $In_2O_3$:$Ga_2O_3$:ZnO is 1:1:2. The filling factor of such a target is greater than or equal to 90% and less than or equal to 100%, preferably greater than or equal to 95% and less than or equal to 99.9%. With the metal oxide target with higher filling factor, the deposited oxide semiconductor film has high density.

It is preferable that a high-purity gas in which impurities such as hydrogen, water, a hydroxyl group, or hydride are removed be used as the sputtering gas for the deposition of the oxide semiconductor film 2530.

The substrate is placed in a deposition chamber under reduced pressure, and the substrate temperature is set to a temperature higher than or equal to 100° C. and lower than or equal to 600° C., preferably higher than or equal to 200° C. and lower than or equal to 400° C. By depositing the oxide semiconductor film while the substrate is heated, the concentration of an impurity included in the deposited oxide semiconductor film can be reduced. Moreover, damage on the film due to sputtering is reduced. Then, residual moisture in the deposition chamber is removed, a sputtering gas from which hydrogen and moisture are removed is introduced, and the above-described target is used, so that the oxide semiconductor film 2530 is formed over the substrate 2505. In order to remove the residual moisture in the deposition chamber, an entrapment vacuum pump, for example, a cryopump, an ion pump, or a titanium sublimation pump is preferably used. As an exhaustion unit, a turbo molecular pump to which a cold trap is added may be used. In the deposition chamber which is evacuated with the cryopump, a hydrogen atom, a compound containing a hydrogen atom, such as water ($H_2O$), (more preferably, also a compound containing a carbon atom), and the like are removed, whereby the concentration of an impurity in the oxide semiconductor film deposited in the deposition chamber can be reduced.

As one example of the deposition condition, the following is employed: the distance between the substrate and the target is 100 mm, the pressure is 0.6 Pa, the direct-current (DC) power is 0.5 kW, and the atmosphere is an oxygen atmosphere (the proportion of the oxygen flow rate is 100%). It is preferable to use a pulse direct-current power because powder substances (also referred to as particles or dust) generated in deposition can be reduced and the film thickness can be uniform.

Then, the oxide semiconductor film 2530 is processed into an island-shaped oxide semiconductor layer by a second photolithography step and an etching step. A resist mask used for the formation of the island-shaped oxide semiconductor layer may be formed by an inkjet method. Formation of the resist mask by an inkjet method needs no photomask; thus, manufacturing costs can be reduced.

In the case where a contact hole is formed in the gate insulating layer 2507, a step of forming the contact hole can be performed at the same time as processing of the oxide semiconductor film 2530.

For the etching of the oxide semiconductor film 2530, wet etching, dry etching, or both of them may be employed. As an etchant used for wet etching of the oxide semiconductor film 2530, for example, a mixed solution of phosphoric acid, acetic acid, and nitric acid, or ITO07N (produced by Kanto Chemical Co., Inc.)) can be used.

Next, first heat treatment is performed on the oxide semiconductor layer. The oxide semiconductor layer can be dehydrated or dehydrogenated by this first heat treatment. This first heat treatment is performed in a nitrogen atmosphere or a rare gas atmosphere of helium, neon, or argon at a temperature higher than or equal to 400° C. and lower than or equal to 750° C., or higher than or equal to 400° C. and lower than the stain point of the substrate. In this embodiment, the substrate is placed in an electric furnace which is one of heat treatment equipment, and heat treatment is performed on the oxide semiconductor layer for one hour at 450° C. in a nitrogen atmosphere, so that a dehydrated or dehydrogenated oxide semiconductor layer 2531 is formed (see FIG. 6B).

The heat treatment equipment is not limited to an electrical furnace, and may have a device for heating an object by heat conduction or heat radiation from a heating element such as a resistance heating element. For example, an RTA (rapid thermal anneal) apparatus such as a GRTA (gas rapid thermal anneal) apparatus or an LRTA (lamp rapid thermal anneal) apparatus can be used. The LRTA apparatus is an apparatus for heating an object by radiation of light (an electromagnetic wave) emitted from a lamp such as a halogen lamp, a metal halide lamp, a xenon arc lamp, a carbon arc lamp, a high pressure sodium lamp, or a high pressure mercury lamp. A GRTA apparatus is an apparatus for heat treatment using a high-temperature gas. As the high temperature gas, an inert gas which does not react with an object to be treated by heat treatment, such as nitrogen or a rare gas like argon, is used.

For example, as the first heat treatment, GRTA may be performed as follows: the substrate is put in an inert gas heated to a high temperature higher than or equal to 650° C. and lower than or equal to 700° C., is heated for several minutes, and is taken out of the inert gas.

In the first heat treatment, it is preferable that water, hydrogen, and the like be not contained in the inert gas introduced into the heat treatment equipment. Alternatively, the purity of the inert gas is preferably greater than or equal to 6N (99.9999%), far preferably greater than or equal to 7N (99.99999%) (that is, the impurity concentration is preferably less than or equal to 1 ppm, far preferably less than or equal to 0.1 ppm).

Further, after the oxide semiconductor layer is heated in the first heat treatment, a high-purity oxygen gas, a high-purity $N_2O$ gas, or an ultra-dry air (the dew point is lower than or equal to −40° C., preferably lower than or equal to −60° C.) may be introduced into the same furnace. The purity of the oxygen gas or the $N_2O$ gas is preferably 6N (99.9999%) or higher, far preferably 7N (99.99999%) or higher (that is, the impurity concentration of the oxygen gas or the $N_2O$ gas is preferably 1 ppm or lower, far preferably 0.1 ppm or lower). In particular, it is preferable not to contain water, hydrogen, and the like. The oxygen gas or the $N_2O$ gas can act to supply oxygen that is a main component material of an oxide semiconductor, which is removed in the impurity removing step by the hydration or hydrogenation treatment. According to this step, the oxide semiconductor layer can be highly purified to be electrically i-type (intrinsic).

The first heat treatment of the oxide semiconductor layer can be performed on the oxide semiconductor film 2530 before being processed into the island-shaped oxide semiconductor layer. In that case, the substrate is taken out from the heat equipment after the first heat treatment, and then a photolithography step is performed thereon.

The first heat treatment may be performed at any of the following timings after the deposition of the oxide semiconductor layer: after a source electrode layer and a drain electrode layer are formed over the oxide semiconductor layer; after an insulating layer is formed over the source electrode layer and the drain electrode layer.

Further, in the case where a contact hole is formed in the gate insulating layer 2507, the step of forming the contact hole may be performed either before or after the first heat treatment is performed on the semiconductor film 2530.

As the oxide semiconductor layer 2513, an oxide semiconductor layer formed as follows may be used: an oxide semiconductor is deposited twice and heat treatment is performed twice for crystallization. Through that process, a thick crystal region where crystals are oriented to the c-axis perpendicular to the film surface can be formed regardless of the base member.

For example, a first oxide semiconductor film with a thickness greater than or equal to 3 nm and less than or equal to 15 nm is deposited, and first heat treatment is performed in a nitrogen, an oxygen, a rare gas, or a dry air atmosphere at a temperature higher than or equal to 450° C. and lower than or equal to 850° C., preferably higher than or equal to 550° C. and lower than or equal to 750° C., so that a first oxide semiconductor film having a crystal region (including a plate-like crystal) in a region including a surface is formed. Then, a second oxide semiconductor film which is thicker than the first oxide semiconductor film is formed, and second heat treatment is performed at a temperature higher than or equal to 450° C. and lower than or equal to 850° C., preferably higher than or equal to 600° C. and lower than or equal to 700° C.

Through that process, crystal growth can be performed wholly in the second oxide semiconductor film from the bottom toward the top, using the first oxide semiconductor film as a seed crystal; accordingly, an oxide semiconductor layer including a thick crystal region can be formed.

Next, a conductive film to be the source and drain electrode layers (including a wiring formed using the same layer as the source and drain electrode layers) is formed over the gate insulating layer 2507 and the oxide semiconductor layer 2531. The conductive film serving as the source and drain electrode layers can be formed using the same material used for the source electrode layer 2405*a* and the drain electrode layer 2405*b* which is described in Embodiment 3.

A third photolithography step is performed to form a resist mask over the conductive film and selective etching is performed thereon, so that the source electrode layer 2515*a* and the drain electrode layer 2515*b* are formed. Then, the resist mask is removed (see FIG. 6C).

Light exposure at the time of the formation of the resist mask in the third photolithography step may be performed using ultraviolet light, KrF laser light, or ArF laser light. The channel length L of a transistor is determined by a pitch between a lower end of the source electrode layer and a lower end of the drain electrode layer, which are adjacent to each other over the oxide semiconductor layer 2531. In the case where light exposure is performed for a channel length L of less than 25 nm, the light exposure at the time of the formation of the resist mask in the third photolithography step may be performed using extreme ultraviolet light having an extremely short wavelength of several nanometers to several tens of nanometers. In the light exposure by extreme ultraviolet light, the resolution is high and the focus depth is large. Therefore, the channel length L of the transistor can be made to greater than or equal to 10 nm and less than or equal to 1000 nm, operation speed of a circuit can be increased, and power consumption can be reduced because the off-state current thereof is extremely small.

In order to reduce the number of photomasks and steps in the photolithography step, the etching step may be performed using a resist mask formed using a multi-tone mask. Light passed through the multi-tone mask has a plurality of intensities, which enables formation of a resist mask having different thicknesses. The shape of the resist mask can be changed by ashing, and therefore, resist masks having different shapes can be formed without performing a photolithography step. Thus, the number of photomasks can be reduced and the number of photolithography steps can also be reduced accordingly, whereby the manufacturing process can be simplified.

Note that it is preferable that the etching condition of the conductive film be optimized so as not to etch and divide the oxide semiconductor layer 2531. However, it is difficult to obtain such an etching condition under which only the conductive film is etched and the oxide semiconductor layer 2531 is not etched at all. In some cases, part of the oxide semiconductor layer 2531 is etched off when the conductive film is etched, to form a groove portion (a recessed portion) in the oxide semiconductor layer.

In this embodiment, since the conductive film is formed using Ti and the oxide semiconductor layer 2531 is formed using an In—Ga—Zn—O-based oxide semiconductor, ammonia hydrogen peroxide (a mixed solution of ammonia, water, and hydrogen peroxide) may be used as an etchant for etching the conductive film.

Next, the insulating layer 2516 serving as a protective insulating film is formed in contact with part of the oxide semiconductor layer. Before the formation of the insulating layer 2516, plasma treatment with the use of a gas of $N_2O$, $N_2$, Ar, or the like may be performed to remove water or the like adsorbed on an exposed surface of the oxide semiconductor layer.

The insulating layer 2516 can be formed to a thickness of at least 1 nm by a method by which impurities such as water or hydrogen do not enter the insulating layer 2516, such as a sputtering method, as appropriate. Hydrogen contained in the insulating layer 2516 might enter the oxide semiconductor layer or extract oxygen in the oxide semiconductor layer. In that case, the resistance of part of the oxide semiconductor layer on the back-channel side might be decreased (the conductivity type of that part might become an n-type) to form a parasitic channel. Therefore, it is important that the insulating layer 2516 is formed by a method by which hydrogen and impurities containing hydrogen do not enter.

In this embodiment, a silicon oxide film is formed to a thickness of 200 nm as the insulating layer 2516 by a sputtering method. The substrate temperature in the film deposition may be set higher than or equal to room temperature and lower than or equal to 300° C. and is 100° C. in this embodiment. The silicon oxide film can be deposited by a sputtering method in a rare gas (typically, argon) atmosphere, an oxygen atmosphere, or a mixed atmosphere containing a rare gas and oxygen. Further, silicon oxide or silicon can be used as a target. For example, with use of silicon as the target, a silicon oxide film can be formed by a sputtering method under an atmosphere containing oxygen. The insulating layer 2516 which is formed in contact with the oxide semiconductor layer is formed using an inorganic insulating film that does not contain impurities such as moisture, a hydrogen ion, and a hydroxyl group and blocks entry of such impurities from the outside. Typically, a silicon oxide film, a silicon oxynitride film, an aluminum oxide film, an aluminum oxynitride film, or the like can be used as the insulating layer 2516.

In order to remove residual moisture in the deposition chamber of the insulating layer 2516 at the same time as deposition of the oxide semiconductor film 2530, an entrapment vacuum pump (such as a cryopump) is preferably used. When the insulating layer 2516 is deposited in the deposition chamber evacuated using a cryopump, the impurity concentration in the insulating layer 2516 can be reduced. In addition, as an exhaustion unit for removing the residual moisture in the deposition chamber of the insulating layer 2516, a turbo-molecular pump provided with a cold trap may be used.

A high-purity gas from which impurities such as hydrogen, water, a hydroxyl group, or hydride are removed is preferably used as a sputtering gas used in the deposition of the insulating layer 2516.

Next, second heat treatment is performed in an inert gas atmosphere or an oxygen gas atmosphere (preferably at 200° C. to 400° C., e.g. at 250° C. to 350° C.). For example, the second heat treatment is performed in a nitrogen atmosphere at 250° C. for one hour. The second heat treatment performs heating while part (a channel formation region) of the oxide semiconductor layer is in contact with the insulating layer 2516.

Through the above process, the first heat treatment is performed on the oxide semiconductor film so that oxygen that is one of main components of an oxide semiconductor and is reduced in addition to the impurities such as hydrogen, moisture, a hydroxyl group, or hydride (also referred to as a hydrogen compound) can be supplied. Accordingly, the oxide semiconductor layer is highly purified and is made to be an i-type (intrinsic) semiconductor.

Figure 6D:
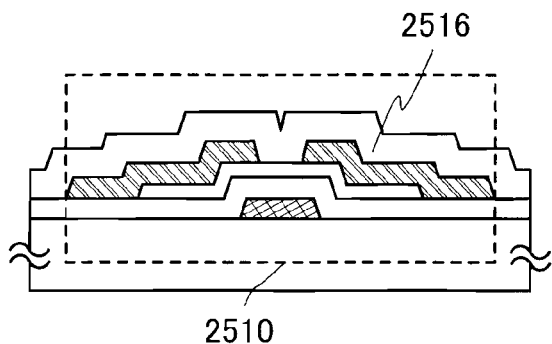
Figure 6E:
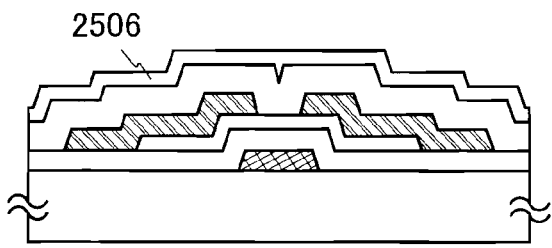

Through the above-described process, the transistor 2510 is formed (see FIG. 6D).

In the case where an oxide silicon layer containing many defects is used as the insulating layer, impurities such as hydrogen, moisture, a hydroxyl group, or hydride contained in the oxide semiconductor layer can be diffused into the oxide silicon layer by the heat treatment after the formation of the silicon oxide layer. That is, the amount of the impurity contained in the oxide semiconductor layer can be further reduced.

A protective insulating layer 2506 may be formed over the insulating layer 2516. For example, a silicon nitride film is formed by a sputtering method. As the protective insulating layer, an inorganic insulating film which contains impurities such as moisture as little as possible and can prevent entering of them from the outside, such as a silicon nitride film or an aluminum nitride film may be used. In this embodiment, a silicon nitride film is used as the protective insulating layer 2506 (see FIG. 6E).

In this embodiment, the silicon nitride film used as the protective insulating layer 2506 is formed as follows: the substrate 2505 provided with the elements up to and including the insulating layer 2516 is heated to a temperature higher than or equal to 100° C. and lower than or equal to 400° C., a sputtering gas containing high-purity nitrogen from which hydrogen and moisture are removed is introduced, and a target of silicon is used. In that case also, it is preferable that residual moisture be removed from the treatment chamber in the formation of the protective insulating layer 2506 as is the case of the insulating layer 2516.

After the formation of the protective insulating layer, heat treatment may be further performed at a temperature higher than or equal to 100° C. and lower than or equal to 200° C. in the air for 1 hour to 30 hours. This heat treatment may be performed at a fixed heating temperature. Alternatively, the following cycle in the heating temperature may be repeated plural times: the temperature is increased from room temperature to a heating temperature and then decreased to room temperature.

In this manner, with the use of the transistor including a highly-purified oxide semiconductor layer manufactured using this embodiment, the current value in an off state (an off-state current) can be further reduced.

Further, with the transistor including a highly-purified oxide semiconductor layer, high field-effect mobility can be obtained, which enables high-speed operation. Accordingly, for example, in a display device or the like, a driver circuit portion can be manufactured over the same substrate as a pixel portion, which leads to reduction of the number of components.

Embodiment 4 can be implemented in combination with any of the other embodiments and examples as appropriate.

(Embodiment 5)

In Embodiment 5, a liquid crystal display device which is an example of a display device according to one embodiment of the present invention will be described.

Figure 7:
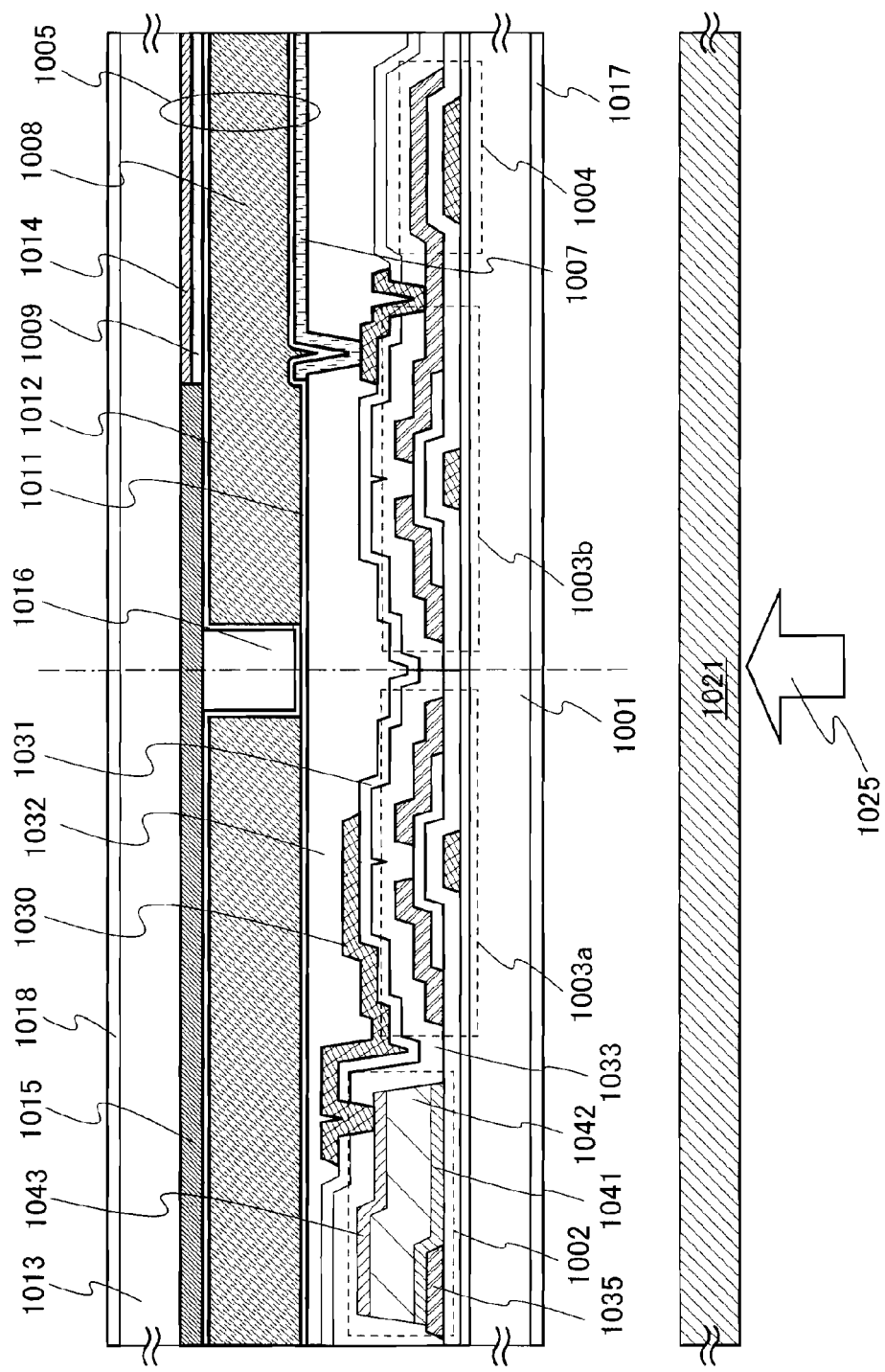
FIG. 7 is a cross-sectional view of a semiconductor device in which a display element portion and a photosensor portion are provided in a display region.

FIG. 7 illustrates an example of a cross-sectional view of a liquid crystal display device. In the liquid crystal display device in this embodiment, a photodiode 1002, transistors 1003*a* and 1003*b*, a storage capacitor 1004, and a liquid crystal element 1005 are provided over a substrate 1001 having an insulating surface. Part of a photosensor and part of a display element are shown respectively on the left side and right side with a dashed-dotted line as a center in FIG. 7. Although FIG. 7 illustrates an example of the structures of the photosensor portion and the display element portion described in Embodiment 1, the configuration of the photosensor portion described in Embodiment 2 may be applied thereto.

As the transistors 1003*a* and 1003*b*, any transistors having the structures described in Embodiment 3 can be used; in this embodiment, inversely staggered transistors are used.

The transistor 1003*a* provided in the photosensor is provided with a back-gate electrode 1030 over a protective insulating film 1031. The back-gate electrode is extended to be electrically connected to a cathode of a photodiode 1002. The back-gate electrode may be formed over an insulating film 1033 without providing the protective insulating film 1031 therebetween.

The photodiode 1002 has a stacked-layer type of PIN junction which includes a p-type semiconductor layer 1041 containing an impurity imparting a p-type conductivity, an i-type semiconductor layer 1042 having characteristics of an intrinsic semiconductor, and an n-type semiconductor layer 1043 containing an impurity imparting an n-type conductivity.

As a typical example thereof, a photodiode in which the i-type semiconductor layer 1042 is formed using amorphous silicon can be given. In that case, the p-type semiconductor layer 1041 and the n-type semiconductor layer 1043 can also be formed using amorphous silicon; however, it is preferable to use microcrystalline silicon possessing high electrical conductivity instead of amorphous silicon. Such a photodiode using the i-type semiconductor layer 1042 formed using amorphous silicon features in that the light absorption property has a luminosity factor which is close to that of human eyes and malfunction by an infrared ray can be prevented.

In this embodiment, the p-type semiconductor layer 1041 which is an anode of the photodiode is electrically connected to a signal wiring 1035 and the n-type semiconductor layer 1043 which is a cathode of the photodiode is, as described above, electrically connected to the back-gate electrode of the transistor 1003*a*. The signal wiring 1035 corresponds to the reset signal line described in Embodiment 1.

A light-transmitting conductive layer may be provided on a light incidence side of the p-type semiconductor layer 1041, though not shown. A conductive layer may be provided on an interface side with the insulating film 1033 of the n-type semiconductor layer 1043. For example, the back-gate electrode 1030 may be extended to cover the n-type semiconductor layer 1043. Such a conductive layer can suppress the loss of electrical charge due to resistance of the p-type semiconductor layer 1041 and/or the n-type semiconductor layer 1043.

Although a PIN diode is illustrated as the photodiode 1002 in this embodiment, the photodiode 1002 may be a PN diode. In that case, it is preferable that a p-type semiconductor layer and an n-type semiconductor layer be formed using high quality crystal silicon.

Figure 8:
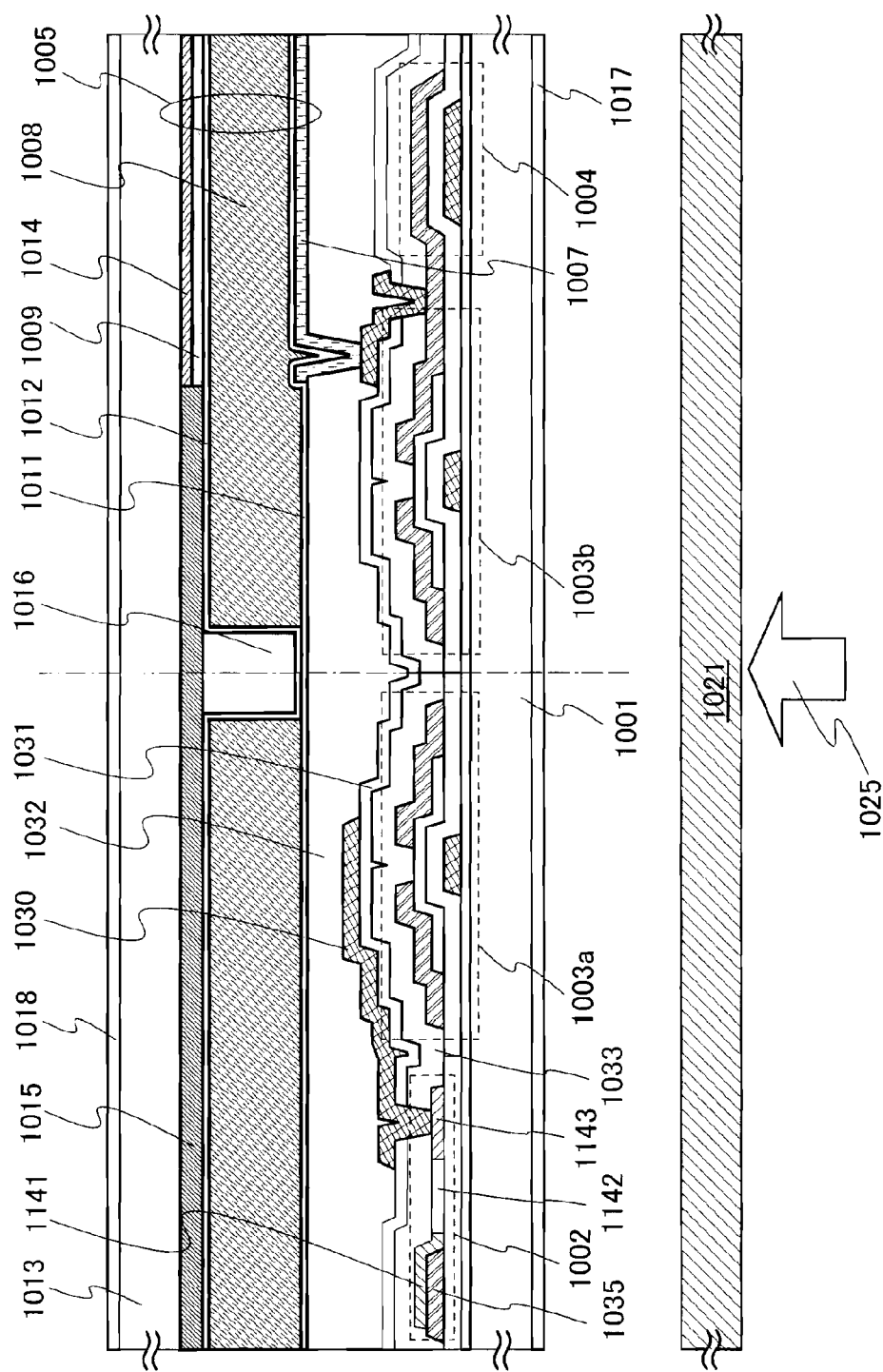
FIG. 8 is a cross-sectional view of a semiconductor device in which a display element portion and a photosensor portion are provided in a display region.

The photodiode may have a structure of a horizontal junction as shown in FIG. 8. In a PIN horizontal junction photodiode, a p-type semiconductor layer 1141, an i-type semiconductor layer 1142, and an n-type semiconductor layer 1143 can be provided as follows: an i-type semiconductor layer is formed, and an impurity imparting a p-type conductivity and an impurity imparting an n-type conductivity are added into parts of the i-type semiconductor layer.

The transistor 1003*b* is provided in the display element to drive the liquid crystal element. One of a source electrode and a drain electrode of the transistor 1003*b* is electrically connected to a pixel electrode 1007, and the other of the source electrode and the drain electrode is, though not shown, electrically connected to the signal wiring.

The storage capacitor 1004 can be formed in the step of forming the transistor 1003*a*, 1003*b*. A capacitor wiring and a capacitor electrode of the storage capacitor 1004 are formed in respective steps of forming a gate electrode of the transistor and for forming a source/drain electrode thereof, and an insulating film which is a capacity of the storage capacitor 1004 is formed in a step of forming a gate insulating film of the transistor. The storage capacitor 1004 is electrically connected to the one of the source electrode and the drain electrode of the transistor 1003*b*, in parallel to the liquid crystal element 1005.

The liquid crystal element 1005 includes a pixel electrode 1007, liquid crystals 1008, and a counter electrode 1009. The pixel electrode 1007 is formed over a planarization insulating film 1032 and is electrically connected to the transistor 1003*b* and the storage capacitor 1004. Further, the counter electrode 1009 is provided for a counter substrate 1013, and the liquid crystals 1008 are provided between the pixel electrode 1007 and the counter electrode 1009.

A cell gap between the pixel electrode 1007 and the counter electrode 1009 can be controlled by using a spacer

1016. Although the cell gap is controlled using the spacer 1016 which is selectively formed by photolithography and has a columnar shape in FIG. 7, the cell gap can alternatively be controlled by sphere spacers provided between the pixel electrode 1007 and the counter electrode 1009. The position of the spacer 1016 in FIG. 7 is an example; the position of the spacer can be decided as appropriate.

Further, the liquid crystals 1008, between the substrate 1001 and the counter substrate 1013, are surrounded by a sealing material. The liquid crystals 1008 may be injected by a dispenser method (droplet method) or a dipping method (pumping method).

The pixel electrode 1007 can be formed using a light-transmitting conductive material such as indium tin oxide (ITO), indium tin oxide containing silicon oxide, organic indium, organic tin, zinc oxide, indium zinc oxide (IZO) containing zinc oxide, zinc oxide containing gallium, tin oxide, indium oxide containing tungsten oxide, indium zinc oxide containing tungsten oxide, indium oxide containing titanium oxide, indium tin oxide containing titanium oxide, or the like.

In addition, since the transparent liquid crystal element 1005 is given as an example in this embodiment, the counter electrode 1009 can also be formed using the above-described light-transmitting conductive material like the pixel electrode 1007.

An alignment film 1011 is provided between the pixel electrode 1007 and the liquid crystals 1008 and an alignment film 1012 is provided between the counter electrode 1009 and the liquid crystals 1008. The alignment film 1011 and the alignment film 1012 can be formed using an organic resin such as polyimide or polyvinyl alcohol. An alignment treatment such as rubbing is performed on their surfaces in order to align liquid crystal molecules in certain direction. Rubbing can be performed by rolling a roller wrapped with cloth of nylon or the like while applying pressure on the alignment film so that the surface of the alignment film is rubbed in certain direction. By using an inorganic material such as silicon oxide, the alignment film 1011 and the alignment film 1012 each having an alignment property can be directly formed by evaporation method without performing an alignment treatment.

Further, a color filter 1014 capable of transmitting light with a particular wavelength is provided for the counter substrate 1013 so as to overlap with the liquid crystal element 1005. The color filter 1014 can be selectively formed as follows: an organic resin such as an acrylic-based resin in which pigment is dispersed is applied over the counter substrate 1013 and is subjected to photolithography. Alternatively, the color filter 1014 can be selectively formed as follows: a polyimide-based resin in which pigment is dispersed is applied over the counter substrate 1013 and is subjected to etching. Further alternatively, the color filter 1014 can be selectively formed by a droplet discharge method such as an ink jet method. The color filter 1014 is not necessarily provided.

Further, a shielding film 1015 capable of shielding light is provided for the counter substrate 1013 so as to overlap with the photodiode 1002. The shielding film 1015 can prevent irradiation on the photodiode 1002 directly with a light of the backlight passing through the counter substrate 1013. In addition, the shielding film 1015 can prevent disclination due to disorder of alignment of the liquid crystals 1008 among pixels from being observed. The shielding film 1015 can be formed using an organic resin containing black colorant such as carbon black or titanium lower oxide. Alternatively, the shielding film 1015 can be formed using a film of chromium.

Further, a polarizing plate 1017 is provided on the side of the substrate 1001, which is opposite to the side over which the pixel electrode 1007 is provided, and a polarizing plate 1018 is provided on the side of the counter substrate 1013, which is opposite to the side over which the counter electrode 1009 is provided.

The liquid crystal element can be a TN (twisted nematic) type, a VA (vertical alignment) type, an OCB (optically compensated birefringence) type, an IPS (in-plane switching) type, or the like. Although the liquid crystal element 1005 in which the liquid crystals 1008 are provided between the pixel electrode 1007 and the counter electrode 1009 is described as an example in this embodiment, the semiconductor device according to one embodiment of the present invention is not limited to this structure. A liquid crystal element in which a pair of electrodes is provided on the substrate 1001 side such as an IPS type liquid crystal element may be employed as well.

Outside light to be detected by the photodiode 1002 enters the substrate 1001 in a direction indicated by an arrow 1025 to reach the photodiode 1002. For example, when an object 1021 to be detected exists, the object 1021 blocks outside light, so that incidence of the outside light into the photodiode 1002 is prevented.

On the other hand, light from the backlight passing through the liquid crystal element 1005 reflects on the object 1021 and the reflected light enters the photodiode 1002. The above-described two actions are opposite to each other; however, whether the object exists or not can be detected by reading a time-oriented change, so that a function as a touch panel can be provided.

Further, an object to be detected may be in close contact with the substrate 1001 and outside light passing through the object or light from the backlight, which is reflected on the object may be detected by the photodiode, so that a function as a contact-type image sensor can be provided.

Embodiment 5 can be implemented in combination with any of the other embodiments and examples as appropriate.
(Embodiment 6)

In Embodiment 6, a liquid crystal display device which is an example of a display device according to one embodiment of the present invention, which is different from Embodiment 5 will be described.

Embodiment 5 can be referred to except for the description made below. For example, transistors, a photodiode, a liquid crystal element, and the like can be formed using the same materials as those in Embodiment 5.

Figure 9:
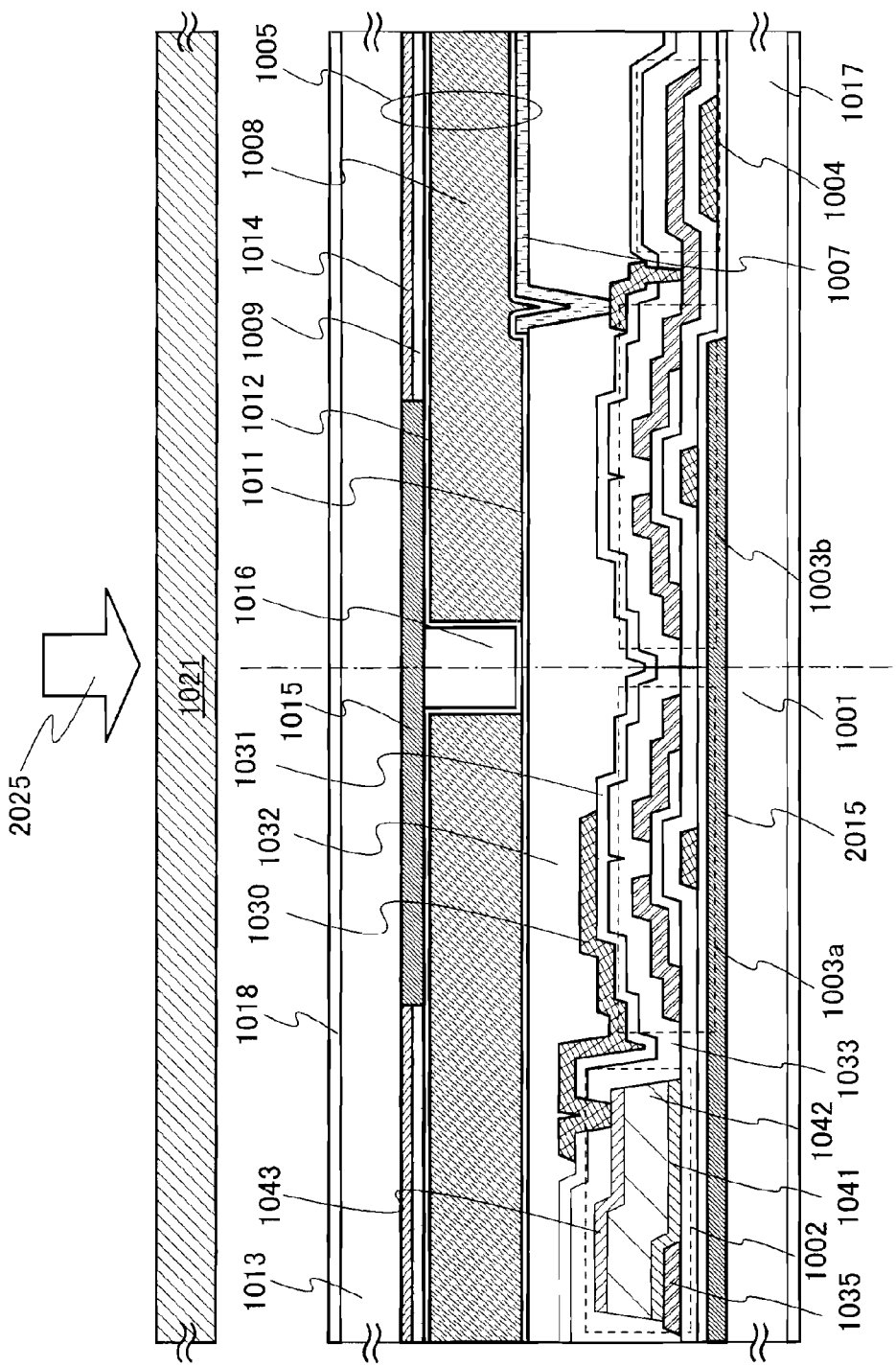
FIG. 9 is a cross-sectional view of a semiconductor device in which a display element portion and a photosensor portion are provided in a display region.

FIG. 9 is an example of a cross-sectional view of the display device which is different from Embodiment 5. Unlike Embodiment 5 in which light enters from the substrate side on which the photosensor is manufactured, light enters a photosensor from the counter substrate side, that is, through a liquid crystal layer in this embodiment.

Therefore, it is necessary to form an opening in a region of a shielding film 1015 provided for a counter substrate 1013, which overlaps with a photodiode 1002. A color filter may be formed in the opening as shown in the drawing. A plurality of photosensors provided with color filters with colors R (red), G (green), and B (blue) may be provided in a pixel circuit to form a color sensor, so that a color image sensor function can be provided.

Although light enters from the p-type semiconductor layer 1041 side of the photodiode 1002 in Embodiment 5, light enters from the n-type semiconductor layer 1043 side in this embodiment with the same structure as Embodiment 5. The reason why light is made to enter from the p-type semiconductor layer side is that holes whose diffusion length is short can be effectively taken out, that is, a larger amount of current can be taken out from the photodiode; light may enter from the n-type semiconductor layer side as long as a design current value is satisfied.

In this embodiment, the p-type semiconductor layer 1041 and the n-type semiconductor layer 1043 may be counterchanged each other in the photodiode 1002, so that light can easily enter from the p-type semiconductor layer side. Note that in that case, the operation method is different from that described in Embodiment 5 because the back-gate electrode 1030 is connected to the transistor 1003*a* on the p-type semiconductor layer (anode) side. Embodiment 1 can be referred to for each operation method.

Figure 10:
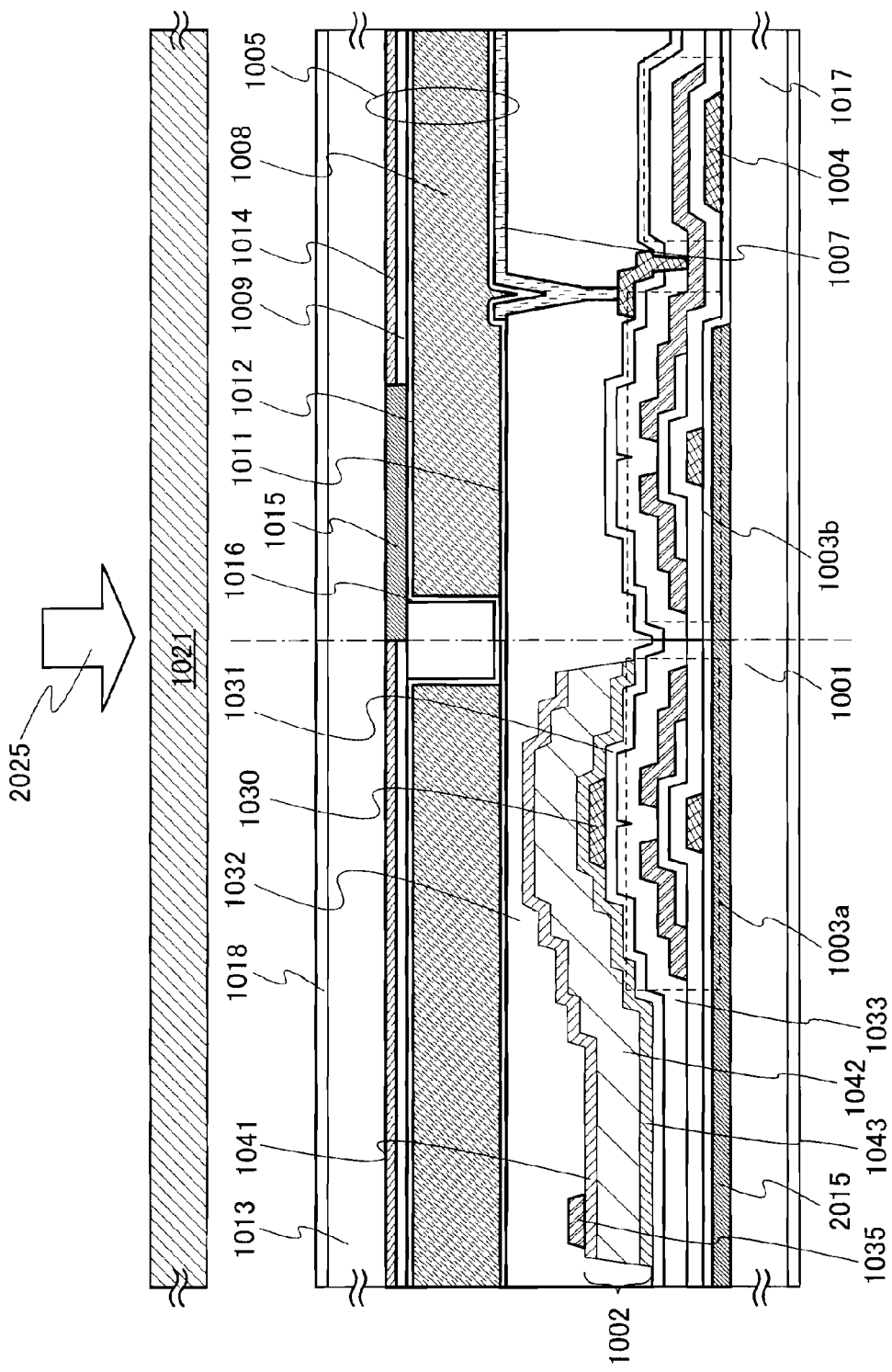
FIG. 10 is a cross-sectional view of a semiconductor device in which a display element portion and a photosensor portion are provided in a display region.

A photodiode 1002 may be formed to overlap with and over a transistor 1003*a* as shown in FIG. 10. In that case, a back-gate electrode 1030 of the transistor 1003*a* can be easily connected to an n-type semiconductor layer 1043 of the photodiode 1002, and light can enter from the p-type semiconductor layer 1041 side. Further, the photodiode can be formed to have a large area, thereby improving the light-receiving sensitivity.

A light-transmitting conductive layer may be provided on the light incidence side of the photodiode 1002 in any of FIG. 9 and FIG. 10, though not shown. A conductive layer may be provided on the side opposite to the light incidence side of the photodiode 1002. Such a conductive layer can suppress the loss of electrical charge due to resistance of the p-type semiconductor layer 1041 and/or the n-type semiconductor layer 1043.

In this embodiment, a shielding film 2015 is provided on the side opposite to the light-receiving side of the photodiode 1002. The shielding film 2015 prevents light from the backlight that passes through a substrate 1001 and enters the display panel from directly reaching the photodiode 1002, so that high-accuracy image pick-up can be performed. An organic resin containing black colorant such as carbon black or titanium lower oxide can be used for the shielding film 2015. Alternatively, the shielding film 2015 can be formed using a film of chromium.

Outside light to be detected by the photodiode 1002 enters the counter substrate 1013 in a direction indicated by an arrow 2025 to reach the photodiode 1002. For example, when an object 1021 to be detected exists, the object 1021 blocks outside light, so that incidence of the outside light into the photodiode 1002 is blocked out.

On the other hand, light from the backlight passing through a liquid crystal element 1005 reflects on the object 1021 and the reflected light enters the photodiode 1002. The above-described two phenomena are opposite to each other; however, whether the object exists or not can be detected by reading a time-oriented change thereof, so that a function as a touch panel can be provided.

Further, an object to be detected may be in close contact with the counter substrate 1013 and outside light passing through the object and/or light from the backlight, which is reflected on the object may be detected by the photodiode, so that a function as a contact-type image sensor can be provided.

Embodiment 6 can be implemented in combination with any of the other embodiments and examples as appropriate.
(Embodiment 7)

In Embodiment 7, an example of a writing board (such as a blackboard or a whiteboard) using a display panel including a photosensor will be described.

Figure 11:
FIG. 11 is a view illustrating an example of an electronic appliance using a semiconductor device according to one embodiment of the present invention.

For example, the display panel including a photosensor is provided at a display panel 9696 in FIG. 11.

The display panel 9696 includes a photosensor and a display element.

In this embodiment, it is possible to write freely with a marker pen or the like on the surface of the display panel 9696.

It is easy to erase letters if the letters are written with a fixer-free marker pen or the like.

In addition, it is preferable that the surface of the display panel 9696 be adequately smooth in order that the ink of the marker pen may be easily removed.

For example, the surface of the panel 9696 is adequately smooth when made using a glass substrate or the like.

Alternatively, a transparent synthetic resin sheet or the like may be attached to the surface of the display panel 9696.

For example, acrylic resin is preferably used as the synthetic resin. In that case, the surface of the sheet of synthetic resin is preferably smooth.

Since the display panel 9696 includes the display element, an image can be displayed on the display panel 9696 and something can be written with the marker pen on the surface of the display panel 9696.

Further, the display panel 9696 includes the photosensor, so that letters written with the marker pen can be read and printed out with a printer or the like connected to the display panel 9696.

Further, since the display panel 9696 includes the photosensor and the display element, by writing text, drawing figures, or the like on the surface of the display panel 9696 with an image displayed, a trail of the marker pen read by the photosensor and the image can be synthesized and displayed on the display panel 9696.

Sensing with resistive touch sensors, capacitive touch sensors, or the like is performed at the same time as writing with a marker pen or the like.

On the other hand, sensing with a photosensor is superior in that sensing can be performed anytime after something is written with a marker pen or the like, even after time passes.

Embodiment 7 can be implemented in combination with any of the other embodiments and examples as appropriate.

EXAMPLE 1

Figure 12:
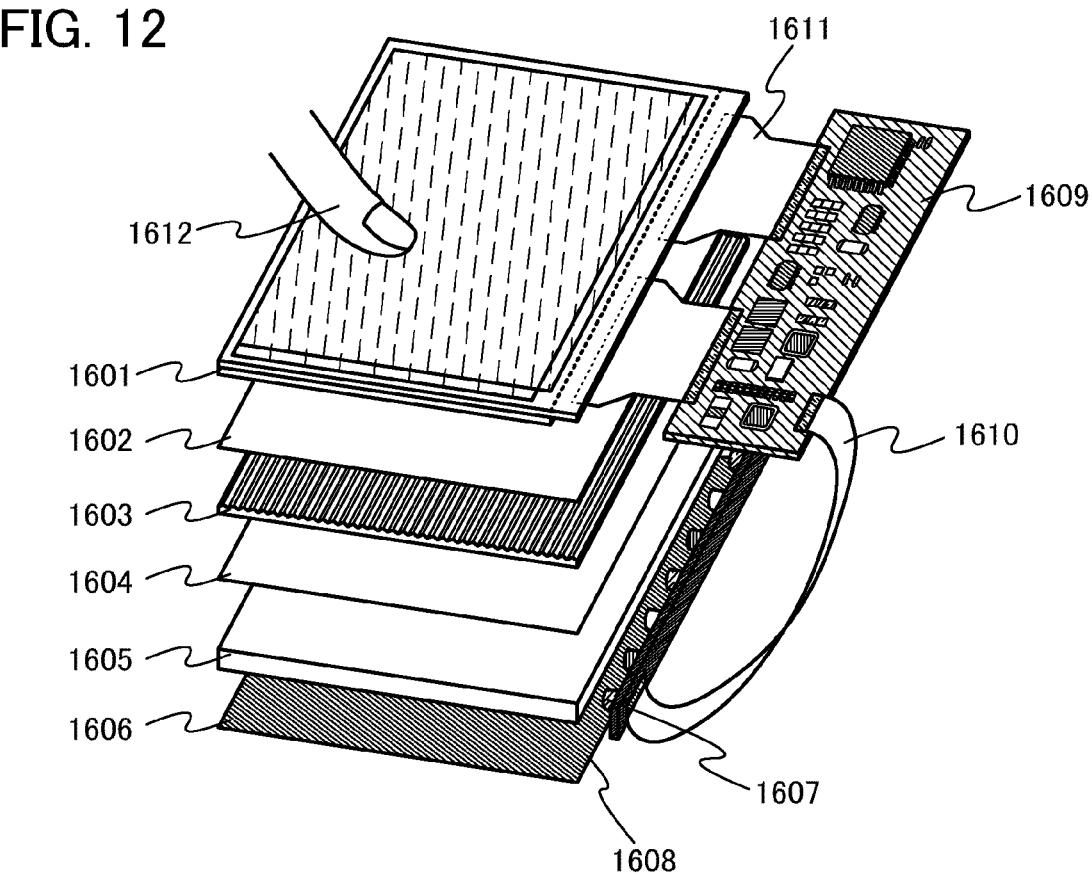
FIG. 12 is a diagram illustrating a structure of a semiconductor device according to one embodiment of the present invention.

In Example 1, positions of a panel and a light source will be described. FIG. 12 illustrates an example of a perspective view of a structure of a display panel according to an embodiment of the present invention. The display panel illustrated in FIG. 12 includes a panel 1601 in which a pixel including a liquid crystal element, a photodiode, a thin film transistor, or the like is provided between a pair of substrates; a first diffusing plate 1602; a prism sheet 1603; a second diffusing plate 1604; a light guide plate 1605; a reflector plate 1606; a backlight 1608 having a plurality of light sources 1607; and a circuit board 1609.

The panel 1601, the first diffusing plate 1602, the prism sheet 1603, the second diffusing plate 1604, the light guide plate 1605, and the reflector 1606 are stacked sequentially. The light sources 1607 are provided at an end portion of the light guide plate 1605. Light from the light sources 1607 diffused into the light guide plate 1605 is uniformly shone from the counter substrate side on the panel 1601 with the use of the first diffusing plate 1602, the prism sheet 1603, and the second diffusing plate 1604.

Although the first diffusing plate 1602 and the second diffusing plate 1604 are used in this example, the number of diffusing plates is not limited thereto. The number of diffusing plates may be one, or may be three or more. The diffusing plate may be provided between the light guide plate 1605 and the panel 1601. Therefore, the diffusing plate may be provided only on the side closer to the panel 1601 than the prism sheet 1603, or may be provided only on the side closer to the light guide plate 1605 than the prism sheet 1603.

Further, the shape of the cross section of the prism sheet 1603, which is shown in FIG. 12, is not limited to serrate; the shape may be any shape as long as light from the light guide plate 1605 can be gathered to the panel 1601 side.

The circuit board 1609 is provided with a circuit for generating or processing various signals to be input to the panel 1601, a circuit for processing various signals to be output from the panel 1601, and the like. In FIG. 12, the circuit board 1609 and the panel 1601 are connected to each other via a flexible printed circuit (FPC) 1611. The above-described circuit may be connected to the panel 1601 by a chip on glass (COG) method, or part of the above-described circuit may be connected to the FPC 1611 by a chip on film (COF) method.

FIG. 12 shows an example in which the circuit board 1609 is provided with a control circuit which controls driving of the light source 1607, where the control circuit and the light source 1607 are connected via the FPC 1610. The above-described control circuit may be provided over the panel 1601; in that case, the panel 1601 and the light source 1607 are connected to each other via an FPC or the like.

Although FIG. 12 illustrates an edge-light type light source in which the light source 1607 is provided at the edge of the panel 1601, a display panel according to one embodiment of the present invention may be a direct-below type display panel in which the light source 1607 is provided directly below the panel 1601.

For example, a finger 1612, an object, gets close to the panel 1601 from above, and part of light that passes through the panel 1601 from the backlight 1608 reflects on the finger 1612 and enters the panel 1601 again. Color image data of the finger 1612 can be obtained by sequentially lighting the light sources 1607 that correspond to individual colors and obtaining image data of every color. Further, the position of the finger 1612 can be recognized from the image data, with which data of a display image can be combined to provide a function as a touch panel.

Example 1 can be implemented in combination with any of the other embodiments and example as appropriate.

EXAMPLE 2

A semiconductor device according to one embodiment of the present invention features in that image data with high resolution can be obtained. Therefore, an electronic appliance using the semiconductor device according to one embodiment of the present invention can be equipped with a higher function.

For example, the semiconductor device according to one embodiment of the present invention can be used for display devices, laptop computers, or image reproducing devices provided with recording media (typically, devices which reproduce the content of recording media such as DVDs (digital versatile discs) and have displays for displaying the reproduced images). Other than the above, as electronic appliances which can be provided with the semiconductor device according to one embodiment of the present invention, there are mobile phones, portable game machines, portable information terminals, e-book readers, video cameras, digital still cameras, goggle-type displays (head mounted displays), navigation systems, audio reproducing devices (e.g., car audio systems and digital audio players), copiers, facsimiles, printers, multifunction printers, automated teller machines (ATM), vending machines, and the like. FIGS. 13A to 13D illustrate specific examples of these electronic appliances.

Figure 13A:
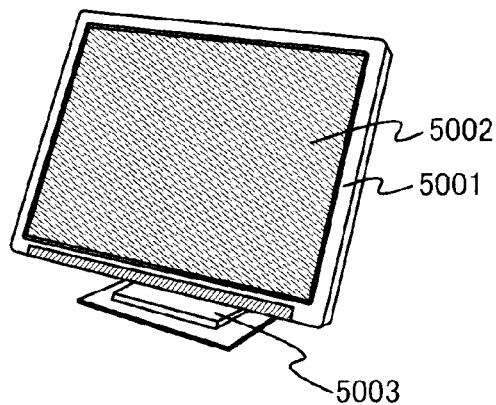
FIGS. 13A to 13D are views illustrating examples of an electronic appliance using a semiconductor device according to one embodiment of the present invention.

FIG. 13A illustrates a display device including a housing 5001, a display portion 5002, a support base 5003, and the like. The display device according to one embodiment of the present invention can be used for the display portion 5002. A semiconductor device according to one embodiment of the present invention used for the display portion 5002 makes it possible to provide a display device capable of obtaining image data with high resolution and capable of being equipped with higher-functional applications. Further, as examples of the display device, any kind of display device for data display for personal computer, TV broadcast reception, advertisement, or the like is included.

Figure 13B:
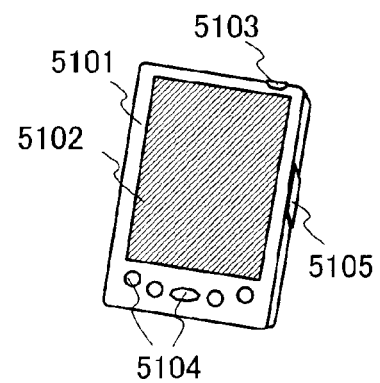

FIG. 13B illustrates a portable information terminal that includes a housing 5101, a display portion 5102, a switch 5103, operation keys 5104, an infrared port 5105, and the like. The semiconductor device according to one embodiment of the present invention can be used for the display portion 5102. The semiconductor device according to one embodiment of the present invention used for the display portion 5102 makes it possible to provide a portable information terminal capable of obtaining image data with high resolution and being equipped with higher-functional applications.

Figure 13C:
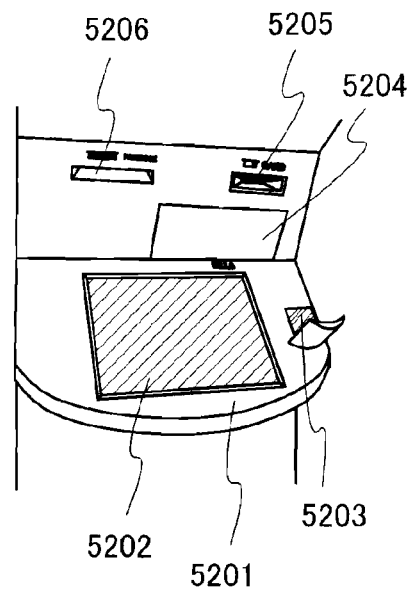

FIG. 13C illustrates an automated teller machine that includes a housing 5201, a display portion 5202, a coin slot 5203, a paper money slot 5204, a card slot 5205, a passbook slot 5206, and the like. The semiconductor device according to one embodiment of the present invention can be used for the display portion 5202. The semiconductor device according to one embodiment of the present invention used for the display portion 5202 makes it possible to provide an automated teller machine capable of obtaining image data with high resolution and being equipped with higher-functional applications. The automated teller machine using the semiconductor device according to one embodiment of the present invention can read information of living body such as a finger print, a face, a handprint, a palm print, a pattern of a hand vein, an iris, and the like which are used for biometrics with higher accuracy. Therefore, a false non-match rate which is false recognition of a person as another person and a false acceptance rate which is false recognition of another person as a person to be identified can be suppressed.

Figure 13D:
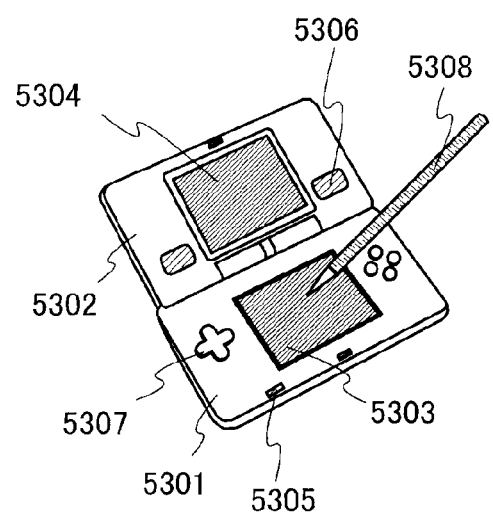

FIG. 13D illustrates a portable game machine including a housing 5301, a housing 5302, a display portion 5303, a display portion 5304, a microphone 5305, a speaker 5306, an operation key 5307, a stylus 5308, and the like. The semiconductor device according to one embodiment of the present invention can be used for the display portion 5303 or the display portion 5304. The semiconductor device according to one embodiment of the present invention used for the display portion 5303 or the display portion 5304 makes it possible to provide a portable game machine capable of obtaining image data with high resolution and being equipped with higher-functional applications. Although the portable game machine illustrated in FIG. 13D has two display portions 5303 and 5304, the number of display portions included in the portable game machine is not limited thereto.

Example 2 can be implemented in combination with any of the other embodiments and example as appropriate.

This application is based on Japanese Patent Application serial No. 2010-028970 filed with Japan Patent Office on Feb. 12, 2010 and Japanese Patent Application serial No. 2010-053647 filed with Japan Patent Office on Mar. 10, 2010, the entire contents of which are hereby incorporated by reference.

The invention claimed is:

1. A semiconductor device comprising:
    a photodiode; and
    a transistor comprising:
        a first gate electrode;
        an oxide semiconductor layer over the first gate electrode; and
        a second gate electrode over the oxide semiconductor layer,
    wherein one electrode of the photodiode is connected to the second gate electrode of the transistor, and
    wherein the other electrode of the photodiode is connected to a reset signal line.

2. The semiconductor device according to claim 1, wherein an off-state current of the transistor is less than or equal to $1 \times 10^{-17}$ A/μm at a room temperature.

3. The semiconductor device according to claim 1, further comprising a selection signal line electrically connected to the first gate electrode of the transistor.

4. The semiconductor device according to claim 1, further comprising a reference signal line electrically connected to one of a source electrode and a drain electrode of the transistor, and an output signal line electrically connected to the other of the source electrode and the drain electrode of the transistor.

5. The semiconductor device according to claim 1, wherein the photodiode and the transistor are included in an image sensor.

6. A semiconductor device comprising a plurality of pixels, at least one pixel in the plurality of pixels comprising:
    a photodiode; and
    a transistor comprising:
        a first gate electrode;
        a first insulating film over the first gate electrode;
        an oxide semiconductor layer over the first insulating film;
        a source electrode and a drain electrode electrically connected to the oxide semiconductor layer;
        a second insulating film over the source electrode and the drain electrode, the second insulating film being in contact with the oxide semiconductor layer in a region between the source electrode and the drain electrode; and
        a second gate electrode over the second insulating film,
    wherein one electrode of the photodiode is electrically connected to the second gate electrode of the transistor.

7. The semiconductor device according to claim 6, wherein an off-state current of the transistor is less than or equal to $1 \times 10^{-17}$ A/μm at a room temperature.

8. The semiconductor device according to claim 6, further comprising a selection signal line electrically connected to the first gate electrode of the transistor.

9. The semiconductor device according to claim 6, further comprising a reset signal line electrically connected to the other electrode of the photodiode.

10. The semiconductor device according to claim 6, further comprising a reference signal line electrically connected to one of the source electrode and the drain electrode of the transistor, and an output signal line electrically connected to the other of the source electrode and the drain electrode of the transistor.

11. The semiconductor device according to claim 6, wherein the photodiode and the transistor are included in an image sensor.

12. A semiconductor device comprising a plurality of pixels, at least one pixel in the plurality of pixels comprising:
    a photodiode; and
    a transistor comprising:
        a first gate electrode as a back gate;
        a first insulating film over the first gate electrode;
        an oxide semiconductor layer over the first insulating film;
        a source electrode and a drain electrode electrically connected to the oxide semiconductor layer;
        a second insulating film over the oxide semiconductor layer, the source electrode and the drain electrode; and
        a second gate electrode over the second insulating film,
    wherein one electrode of the photodiode is electrically connected to the first gate electrode of the transistor.

13. The semiconductor device according to claim 12, wherein an off-state current of the transistor is less than or equal to $1 \times 10^{-17}$ A/μm at a room temperature.

14. The semiconductor device according to claim 12, further comprising a selection signal line electrically connected to the second gate electrode of the transistor.

15. The semiconductor device according to claim 12, further comprising a reset signal line electrically connected to the other electrode of the photodiode.

16. The semiconductor device according to claim 12, further comprising a reference signal line electrically connected to one of the source electrode and the drain electrode of the transistor, and an output signal line electrically connected to the other of the source electrode and the drain electrode of the transistor.

17. The semiconductor device according to claim 12, wherein the photodiode and the transistor are included in an image sensor.

18. A semiconductor device comprising:
    a photodiode;
    a first transistor comprising:
        a first gate electrode;
        an oxide semiconductor layer over the first gate electrode; and
        a second gate electrode over the oxide semiconductor layer; and
    a second transistor,
    wherein one electrode of the photodiode is connected to the second gate electrode of the first transistor via a first terminal and a second terminal of the second transistor, and
    wherein the other electrode of the photodiode is connected to a reset signal line.

19. The semiconductor device according to claim 18, wherein the second transistor comprises an oxide semiconductor layer.

* * * * *